United States Patent
Chen et al.

(10) Patent No.: US 10,436,792 B2
(45) Date of Patent: Oct. 8, 2019

(54) URINALYSIS DEVICE AND DRY REAGENT FOR QUANTITATIVE URINALYSIS

(71) Applicant: Nitto Denko Corporation, Osaka (JP)

(72) Inventors: Xiaojun Chen, Synapse (SG); Yingsong Wang, Synapse (SG); Pei Shan Ho, Synapse (SG); Xi Er Yeo, Synapse (SG)

(73) Assignee: Nitto Denko Corporation (JP)

( * ) Notice: Subject to any disclaimer, the term of this patent is extended or adjusted under 35 U.S.C. 154(b) by 232 days.

(21) Appl. No.: 15/121,808

(22) PCT Filed: Jun. 10, 2014

(86) PCT No.: PCT/SG2014/000269
§ 371 (c)(1),
(2) Date: Aug. 26, 2016

(87) PCT Pub. No.: WO2015/130225
PCT Pub. Date: Sep. 3, 2015

(65) Prior Publication Data
US 2017/0010276 A1 Jan. 12, 2017

Related U.S. Application Data

(60) Provisional application No. 61/946,228, filed on Feb. 28, 2014.

(51) Int. Cl.
*G01N 33/68* (2006.01)
*G01N 33/70* (2006.01)
(Continued)

(52) U.S. Cl.
CPC ....... *G01N 33/6827* (2013.01); *G01N 21/272* (2013.01); *G01N 21/78* (2013.01);
(Continued)

(58) Field of Classification Search
CPC .. G01N 21/272; G01N 21/78; G01N 2496/00; G01N 33/68; G01N 33/6827;
(Continued)

(56) References Cited

U.S. PATENT DOCUMENTS 3,533,749 A * 10/1970 Kleinman .......... G01N 33/6839
436/88
3,705,013 A 12/1972 Dewhurst
(Continued)

FOREIGN PATENT DOCUMENTS

| CN | 101221183 A | 7/2008 |
|---|---|---|
| CN | 103278648 A | 9/2013 |

(Continued)

OTHER PUBLICATIONS

Bacon et al.: "Kinetic Study ofthe Jaffe Reaction for Quantifying Creatinine in Serum: 2. Evaluation of Buffered Reagent and Comparison of Different Data-Processing Options", Clinical Chemistry, 1989, vol. 35, No. 3, pp. 360-363.
(Continued)

*Primary Examiner* — Maureen Wallenhorst
(74) *Attorney, Agent, or Firm* — Lerner, David, Littenberg, Krumholz & Mentlik, LLP

(57) ABSTRACT

A method of quantitatively determining the concentration of at least one analyte in a sample. The method may involve adding a portion of the sample to a first analyte assay formulation and to an analyte assay reference formulation to generate a first analyte sample and analyte reference sample, and determining the concentration of the at least one analyte in the sample. The method may additionally or alternatively involve adding a portion of the sample to a second analyte assay formulation, and determining the concentration of the at least one analyte in the sample, or both. The method may
(Continued)

Figure 1:
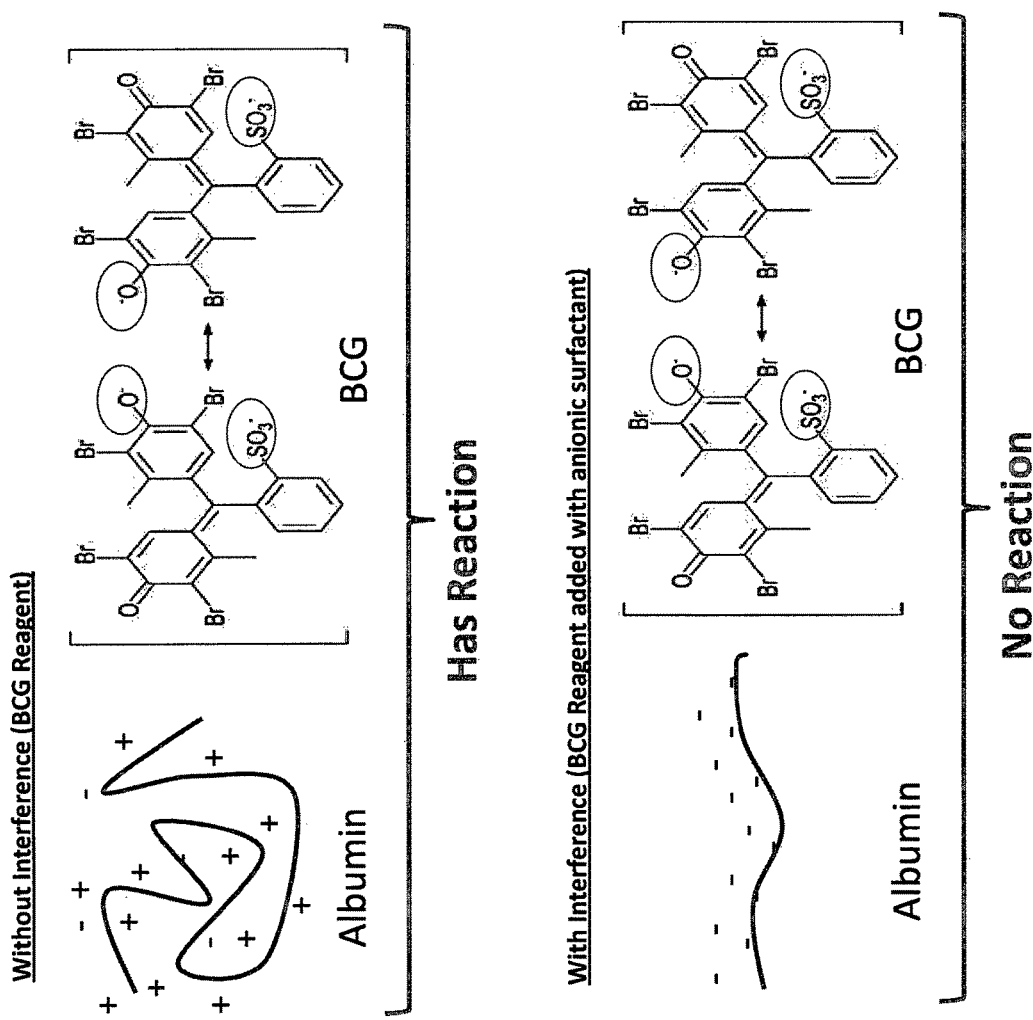

be associated with various formulations, kits of parts, systems and computer implemented methods.

29 Claims, 16 Drawing Sheets

(51) Int. Cl.
*G01N 33/493* (2006.01)
*G01N 33/52* (2006.01)
*G01N 21/78* (2006.01)
*G01N 21/27* (2006.01)

(52) U.S. Cl.
CPC ........... *G01N 33/70* (2013.01); *G01N 33/493* (2013.01); *G01N 2496/00* (2013.01); *Y10T 436/147777* (2015.01)

(58) Field of Classification Search
CPC ................. G01N 33/70; G01N 33/493; Y10T 436/147777; Y10T 436/25375
USPC ................ 436/63, 86, 88, 98, 164, 166, 177
See application file for complete search history.

(56) References Cited

U.S. PATENT DOCUMENTS

| | | | |
|---|---|---|---|
| 3,894,843 A | 7/1975 | Jarvis | |
| 4,111,657 A | 9/1978 | Denney et al. | |
| 4,330,296 A * | 5/1982 | Jain | G01N 33/6839 436/88 |
| 4,529,708 A | 7/1985 | Stephens | |
| 4,568,647 A * | 2/1986 | Sanford | G01N 33/6839 422/420 |
| 4,950,611 A | 8/1990 | Seaton | |
| 5,013,527 A | 5/1991 | Arai et al. | |
| 5,110,746 A * | 5/1992 | Grey | G01N 33/6827 436/34 |
| 5,194,390 A | 3/1993 | Lau | |
| 5,268,146 A | 12/1993 | Lawrence et al. | |
| 5,558,834 A | 9/1996 | Chu et al. | |
| 6,848,196 B2 | 2/2005 | Brulls | |
| 2005/0266574 A1 | 12/2005 | Kosaka | |
| 2011/0076703 A1 | 3/2011 | Borg et al. | |
| 2011/0124120 A1 | 5/2011 | Kranz et al. | |
| 2013/0078738 A1 | 3/2013 | Watanabe et al. | |

FOREIGN PATENT DOCUMENTS

| | | |
|---|---|---|
| EP | 1362925 A1 | 11/2003 |
| JP | S55029718 A | 3/1980 |
| JP | S58172554 A | 10/1983 |
| JP | 3249522 B2 | 1/2002 |
| JP | 2011-522250 A | 7/2011 |
| JP | 2013-83632 A | 5/2013 |
| WO | 1984003948 A1 | 10/1984 |
| WO | 1988010429 A1 | 12/1988 |

OTHER PUBLICATIONS

Schifreen et al.: "Diethylamine Prevents Precipitation in the Alkaline Buffer Reagent for the Kinetic Jaffe Determination of Serum Creatinine", Clinical Chemistry, 1981, vol. 27, No. 1, pp. 196-197.
Nozaki Y. et al.: "The Interaction of a Cationic Detergent with Bovine Serum Albumin and Other Proteins", The Journal of Biological Chemistry, 1974, vol. 249, No. 14, pp. 4452-4459.
International Search Report for Application No. PCT/SG2014/000269 dated Sep. 17, 2014.
Cho M.-C. et al., "Evaluation of the URiSCAN super cassette ACR semiquantitative urine dipstick for microalbuminuria screening : Evaluation of urine dipstick for microalbuminuria screening", J. Clin. Lab. Anal., (Feb. 27, 2014), vol. 28, No. 4, pp. 281-286.
McTaggart M.P. et al., "The diagnostic accuracy of a urine albumin-creatinine ratio point-of-care test for detection of albuminuria in primary care", Am. J. Kidney Dis., (Nov. 2012), vol. 60, No. 5, pp. 787-794.
Parsons M.P. et al., "Validation of a point-of-care assay for the urinary albumin:creatine ratio", Clin. Chem., (Mar. 1999), vol. 45, No. 3, pp. 414-415.
Omoruyi F.O. et al., "Evaluation of the performance of urine albumin, creatinine and albumin-creatinine ratio assay on two POCT analyzers relative to a central laboratory method", Clin. Chim. ACTA, (Dec. 22, 2011), vol. 413, No. 5, pp. 625-629.
Waugh J. et al., "Validation of the DCA 2000 microalbumin: creatinine ratio urinanalyzer for its use in pregnancy and preeclampsia", Hypertension in Pregnancy, (2003), vol. 22, No. 1, pp. 77-92.
Extended European Search Report and subsequent Communication for corresponding EP application No. 14883985.5, dated Oct. 6, 2017.
Communication pursuant to Article 94(3) EPC in EP Application 14883985.5; dated Jan. 21, 2019, 7 pages.
Second Office Action in counterpart Chinese application 2014800765919, dated May 2, 2018, 6 pages, with English Translation.
First Office Action in Application CN 201480076591.9, 8 pages, dated Sep. 15, 2017, with partial English translation.
Office Action dated Jan. 15, 2019 in corresponding Japanese application No. 2016-554178, 3 pages, with English translation.
Office action dated Nov. 27, 2018 in corresponding Japanese application No. 2016-554178, 3 pages, with English translation.
Office action dated May 29, 2018 in corresponding Japanese application No. 2016-554178, 5 pages, with English translation.
Japanese Office Action for JP Application No. 2018141130, dated Apr. 9, 2019.
Japanese Office Action for JP Application No. 2018141131, dated Apr. 9, 2019.

* cited by examiner

Fig. 10
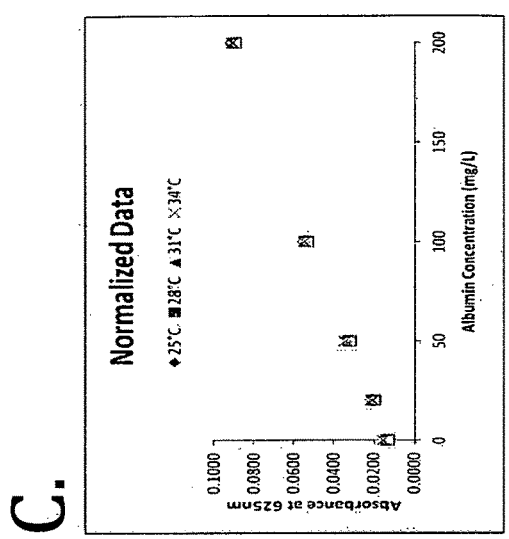
C. Normalized Data
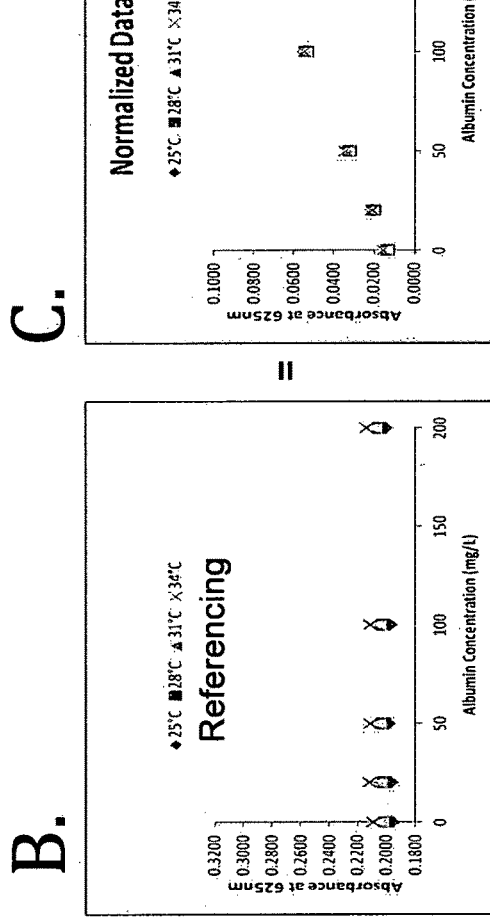
B. Referencing
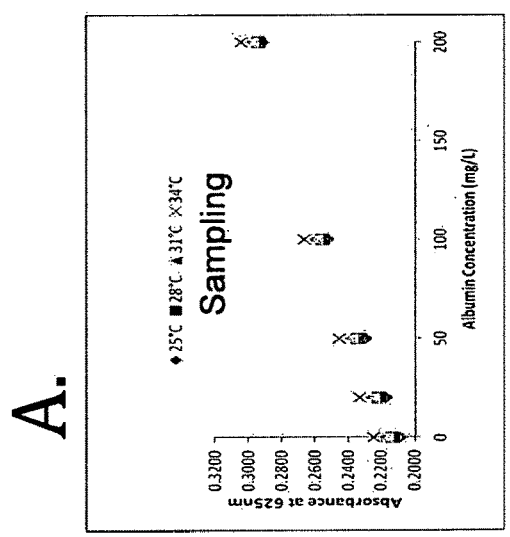
A. Sampling

URINALYSIS DEVICE AND DRY REAGENT FOR QUANTITATIVE URINALYSIS

CROSS REFERENCE TO RELATED APPLICATIONS

The present application is a national phase entry under 35 U.S.C. § 371 of International Application No. PCT/SG2014/000269, filed Jun. 10, 2014, published in English which claims priority from U.S. Patent Application No. 61/946,228, filed Feb. 28, 2014, the disclosures of which are incorporated by reference herein.

BACKGROUND

Urinalysis is a source of information about the anatomy and function of the kidneys and urinary tract. It provides insights into the status of systemic diseases such as diabetes mellitus. The use of test strips, or dipsticks, for urinalysis is widely accepted for health screening purposes because it provides a simple protocol and is very cost-effective.

Dipstick urinalysis is convenient, but false-positive and false-negative results can occur due to the discrimination of color change when it is performed by a human eye, such as by a nurse.

Chronic Kidney Disease (CKD) can be diagnosed in its early stages by a microalbuminuria measurement. The "golden standard" for quantitative measurement of microalbuminuria is from a 24-hour urine collection, but this is very time-consuming and troublesome for patients. Instead, a random spot urine test is most commonly used to screen microalbuminuria, which requires measuring the urine albumin creatinine ratio (ACR), using creatinine to compensate for variations in urine concentration in urine samples.

ACR is also a useful parameter to measure for use as a prognosis factor for kidney failure risk. Monitoring the ACR value during treatment is also useful, and a point-of-care device is required to improve patients' Quality of Life (QOL).

Currently, most of the point-of-care devices available in the market for urinalysis are semi-quantitative and use a test strip and strip reader. A quantitative point-of-care device is desired for home or clinical use.

For example, quantitative urinalysis results can be obtained by using an automatic urine analyzer at the hospital and in a clinical laboratory. A urine analyzer is generally a desk-top machine or part of a larger piece of equipment, such as a fully automated blood serum/urine analyzer. Therefore, the accessibility of these quantitative urinalysis units is centralized and people who live in rural areas have limited access to proper diagnostic tests.

Urine samples have a large pH variation, and the measurement results are also affected by the temperature of the surroundings (i.e. the testing place). Current quantitative assay methods require sample dilution to remove the interference caused by urine. In addition, colorimetric wet reagents for urinalysis are required to be kept in refrigerator, which is not suitable for home or clinical use.

As indicated above, to minimise the effect of pH or interference in current quantitative systems, a urine sample is diluted with a volume of buffer in addition to a strong acid or a strong alkali. To minimise the effect of temperature in the testing room, a cooling system is introduced into the device used for analysis, but this cooling system makes the device bulky. The size of the resulting device makes it difficult to transport and renders it unusable in anything other than a clinical laboratory setting.

In addition, the reagents used in urinalysis may suffer from bubble formation, either occurring during the reaction, or from the addition of the sample to the reagent. This can result in the loss of accuracy due to light scattering.

For current quantitative devices, an internal reference table is normally prepared under a range of pH and/or temperature conditions, so as to normalize the data, but it is troublesome to prepare the reference table and there is a limit on how far the normalisation can be taken, depending on the type of interference. Given this, the result is not accurate for all patients.

As will be appreciated, these problems arise, at least in part, because of the reagents used in the currently available tests.

Given the above, there remains a need for more accurate urinalysis equipment that is portable and which is cost-effective. In addition, there remains a need for analytical reagents that are capable of being tailored for use with a simplified device and which help to increase the accuracy of the result.

SUMMARY OF INVENTION

Aspects and embodiments of the invention are set out in claims 1 to 63, and are considered in more detail below.

In a first aspect of the invention, there is provided a method of quantitatively determining the concentration of at least one analyte in a sample, the method comprising the steps of:
  i) (a) adding a portion of the sample to a first analyte assay formulation comprising a first analyte complexing reagent to generate a first analyte sample;
     (b) adding a portion of the sample to an analyte assay reference formulation that is identical to the first analyte assay formulation, except that it further comprises a reagent that denatures the analyte or blocks the formation of a complex between the analyte and the first analyte complexing reagent, to generate an analyte reference sample; and
     (c) determining the concentration of the at least one analyte in the sample by measuring the absorbance spectra of the first analyte sample and analyte reference sample, calculating the difference between the absorbance spectra of the first analyte sample and the analyte reference sample and comparing the difference spectrum obtained to a first pre-determined calibration curve of analyte concentration;
  and/or
  ii) (a) adding a portion of the sample to a second analyte assay formulation comprising a second analyte complexing reagent to generate a second analyte sample; and
     (b) determining the concentration of the at least one analyte in the sample by measuring the absorbance spectra of the analyte in the second analyte sample over a period of time, calculating the rate of the absorbance change of the second analyte sample over said period of time and comparing the rate obtained to a second pre-determined calibration curve of analyte concentration.

In an embodiment of the invention, the at least one analyte is albumin and the method comprises the steps of:
  adding a portion of the sample to each of an:
  A) albumin assay sample formulation comprising an albumin complexing reagent to generate an albumin sample; and B) albumin assay reference formulation that is identical to the albumin assay formulation except that it further comprises an anionic surfactant to generate an albumin reference sample, and determining the concentration of albumin in the sample by measuring the absorbance spectra of the albumin sample and the albumin reference sample, calculating the difference between the absorbance spectra of the albumin sample and the albumin reference sample and comparing the difference spectrum obtained to a pre-determined calibration curve of albumin concentration.

In an alternative embodiment of the invention, the at least one analyte is creatinine and the method comprises the steps of adding a portion of the sample to a creatinine assay sample formulation comprising a creatinine complexing reagent to generate a creatinine sample and determining the concentration of creatinine in the sample by measuring the change of the absorbance spectra of the creatinine sample over a period of time, calculating the rate of the absorbance change of the creatinine sample over said period of time and comparing the rate obtained to a pre-determined calibration curve of creatinine concentration.

In a further embodiment of the invention, the at least one analyte is albumin and creatinine, the method comprising the steps of:
  a) determining the concentration of creatinine in the sample in accordance with the methods defined above; and
  b) determining the concentration of albumin in the sample in accordance with the methods defined above; and
  further comprising the step of determining the albumin/creatinine ratio of the sample.

In certain embodiments of the invention, one or more of the formulations may be lyophilised. For example, all of the formulations are lyophilised.

In certain embodiments of the invention, the sample is a urine sample.

In further embodiments of the invention, the step of determining the concentration of albumin requires measuring the absorbance spectra:
  at 625 nm of the albumin sample and albumin reference sample; and/or
  at time of about 5 minutes from the addition of the sample to the desired analyte formulation.

In yet further embodiments, the step of determining the concentration of creatinine requires measuring the rate of absorbance change at 525 nm of the creatinine sample.

In yet further embodiments, the step of determining the concentration of creatinine requires measuring the rate of absorbance change at 525 nm of the creatinine sample involves measuring the absorbance during a period of from about 10 seconds up to about 10 minutes. For example, such kinetic measurement starts at 30 seconds and ends at 10 minutes from the addition of the sample to the second assay formulation or the creatinine assay formulation (i.e. the kinetic measurement starts at 1 minute and ends at a time between 5 and 10 minutes from the addition of the sample to the second assay formulation or the creatinine assay formulation).

In yet further embodiments of the invention, the method may determine the creatinine concentration and the albumin concentration simultaneously.

In further embodiments of the invention, the creatinine sample assay formulation is as defined in the second aspect of the invention.

In yet still further embodiments of the invention, the albumin assay formulation is as defined in the third aspect of the invention.

In further embodiments of the invention, the pre-determined calibration curve of albumin concentration is obtained by a computer-implemented method of generating a calibration curve for use in quantitatively determining the concentration of albumin in a urine sample, the method being defined in the sixth aspect of the invention.

In a second aspect of the invention, there is provided a formulation for use in the analysis of the creatinine concentration of a sample comprising:
  a strong base in a concentration of from about 40 to about 80 g/L;
  a buffer in a concentration of from about 50 to about 250 g/L;
  at least one surfactant in a concentration of from about 0.1 to about 20 g/L;
  and water.

In an embodiment of the invention, the formulation further comprises a compound that reacts with creatinine to generate a creatinine complex. For example the compound that reacts with creatinine to generate a creatinine complex is picric acid or, more particularly, dinitrobenzoic acid.

In certain embodiments, the concentration of the compound that reacts with creatinine to generate a creatinine complex is from about 1 to about 5 g/L.

In further embodiments of the invention, the at least one surfactant comprises an anionic surfactant in a concentration from about 0.1 to about 10 g/L and a cationic surfactant in a concentration from about 0.1 to about 10 g/L.

In certain embodiments, the ratio of cationic surfactant:anionic surfactant is from 1:2 to 1:10 (e.g. from 1:3 to 1:7, such as 1:5).

In certain embodiments of the invention, in relation to the formulation for use in the analysis of the creatinine concentration of a sample:
  (a) when the at least one surfactant comprises a cationic surfactant, it is selected from one or more of the group consisting of cetylpyridinium chloride, benzalkonium chloride, benzethonium chloride, dimethyldioctadecyl-ammonium chloride, cetrimonium bromide, dioctadecyldimethylammonium bromide, and hexadecyltrimethylammonium bromide; and/or
  (b) when the at least one surfactant comprises an anionic surfactant, it is selected from one or more of the group consisting of sodium dodecyl sulfate, polystyrene sulfonates, linear alkylbenzene sulfonate, secondary alcohol sulfonate, alcohol olefin sulfonate, and alcohol sulfate; and/or
  (c) the buffer is selected from one or more of the group consisting of $K_2HPO_4$, $Na_2HPO_4$, and borate; and/or
  (d) the strong base is NaOH and/or KOH.

In certain embodiments of the invention, the formulation for use in the analysis of the creatinine concentration of a sample is lyophilised.

In yet further embodiments of the invention, the formulation for use in the analysis of the creatinine concentration of a sample further comprises a bulking agent in an amount of from about 1 to about 40 weight % of the formulation, optionally wherein the bulking agent is selected from one or more of the group consisting of sugar-mannitol, lactose, and trehalose.

In still further embodiments of the invention, the formulation for use in the analysis of the creatinine concentration of a sample, the concentration ratio of the buffer:strong base in the formulation is from 0.5:1 to 2.5:1, such as from 1:1 to 1.5:5, such as 1.25:1.

In a third aspect of the invention, there is provided a formulation for use in the analysis of albumin concentration of a sample comprising:
- a compound that reacts with albumin to generate an albumin complex in a concentration of from about 0.1 to about 1.5 g/L;
- a strong base in a concentration of from about 10 to about 50 g/L;
- a buffer in a concentration of from about 50 to about 250 g/L;
- a first non-ionic surfactant in a concentration of from about 1 to about 20 g/L;
- a preservative in a concentration of from about 0.1 to about 3 g/L; and
- water.

In embodiments of the invention, the formulation further comprises an anionic surfactant. In certain embodiments, the anionic surfactant is present in from about 0.1 to 5 weight % of the formulation. For example, the anionic surfactant is selected from one or more of the group consisting of sodium dodecyl sulfate, polystyrene sulfonates, linear alkylbenzene sulfonate, secondary alcohol sulfonate, alcohol olefin sulfonate, and alcohol sulfate.

In certain embodiments of the invention, the compound that reacts with albumin to generate an albumin complex is bromocresol green.

In certain embodiments of the invention, in relation to the formulation for use in the analysis of the albumin concentration of a sample:
(a) the buffer is selected from one or more of the group consisting of N-(1-acetamido)-2-aminoethanesulfonic acid, sodium acetate, N-(2-acetamido)-iminodiacetic acid, 2-amino-2-methyl-1-propanol, 2-amino-2-methyl-1,3-propanediol, N-(1,1-dimethyl-2-hydroxyethyl)-3-amino-2-hydroxpropanesulfonic acid, N,N-bis-(2-hydroxyethyl)-2-aminoethane-sulfonic acid, sodium hydrogen carbonate, N,N-bis-(2-hydroxyethyl)-glycine, bis-(2-hydroxyethyl)-imino-tris-(hydroxymethyl)-methane, 1,3-bis-[tris-(hydroxymethyl)-methylamino]-propane, 3-cyclohexylamino)-1-propanesulfonic acid, 3-(cyclohexylamino)-2-hydroxy-1-propanesulfonic acid, 2-(N-cyclohexylamine)-ethanesulfonic acid, tri-sodium citrate, N,N-bis-(2-hydroxyethyl)-3-amino-2-hydroxypropanesulfonic acid, 4-(2-hydroxyethyl)pipera-zine-1-ethanesulfonic acid, 4-(2-hydroxyethyl)-piperazine-1-propanesulfonic acid, 4-(2-hydroxyethyl)-piperazine-1(2-hydroxy)-propane-sulfonic acid, 2-morpholinoethanesulfonic acid, 3-morpholinopropanesulfonic acid, 3-morpholino-2-hydroxypropanesulfonic acid, piperazine-1,4-bis-(2-ethanesulfonic acid), piperazine-1,4-bis-(2-hydroxy-propanesulfonicacid), N-[tris-(hydroxymethyl)-methyl]-3-aminopropanesulfonic acid, N-[tris-(hydroxymethyl)-methyl]-3-amino-2-hydroxypropanesulfonic acid, N-[tris-(hydroxymethyl)-methyl]-2-aminoethanesulfonic acid, N-[tris-(hydroxymethyl)-methyl]-glycine, tris-(hydroxy-methyl)-aminomethane, and succinic acid; and/or
(b) the first non-ionic surfactant is selected from one or more of the group consisting of brij, poly(propylene glycol), polyethylene glycol hexadecyl ether, triton X-100, tween, Zonyl™ FSN fluorosurfactant, ALKA-NOL™ 6112 surfactant, polyethylene glycol, optionally wherein the first non-ionic surfactant is brij; and/or
(c) the preservative is selected from one or more of the group consisting of sugar, sorbic acid, benzoic acid, calcium propionate, sodium nitrite, sodium azide, sulfites, disodium EDTA and antioxidants; and/or
(d) the strong base is NaOH and/or KOH.

In further embodiments of the invention, the formulation for use in the analysis of the albumin concentration (and the reference sample) may be lyophilised.

In certain embodiments of the invention, the formulation may further comprise a second non-ionic surfactant in an amount of from about 10 to about 200 g/L of the formulation. For example, the second non-ionic surfactant may be selected from one or more of the group consisting of brij, poly(propylene glycol), polyethylene glycol hexadecyl ether, triton X-100, tween, Zonyl™ FSN fluorosurfactant, ALKANOL™ 6112 surfactant, polyethylene glycol, provided that the first and second non-ionic surfactants are different to each other, optionally wherein the second non-ionic surfactant is polyethylene glycol.

In a fourth aspect of the invention, there is provided a method of preparing the lyophilised formulation for use in the analysis of creatinine concentration of a sample, as described in respect of the second aspect of the invention or the lyophilised formulation for use in the analysis of albumin concentration of a sample as described in the third aspect of the invention, comprising the steps of:
(a) mixing the prescribed chemical components together, filtering the resultant mixture, dispensing said mixture into a container and inserting the container into a freeze drying apparatus;
(b) freezing the sample at a temperature of from about −20° C. to about −80° C. for a period of time ranging from about 0.5 hours to 5 hours;
(c) annealing the sample at a temperature of from about −10° C. to about −30° C. for a period of time ranging from about 1 hour to 5 hours;
(d) re-freezing the sample at a temperature of from about −20° C. to about −80° C. for a period of time ranging from about 0.5 hours to 5 hours;
(e) conducting a first drying cycle at a temperature of from about −10° C. to about −30° C. for a period of time ranging from about 5 hours to 50 hours; and
(f) conducting a second drying cycle at a temperature of from about 0° C. to about 60° C. for a period of time ranging from about 1 hour to 20 hours.

In certain embodiments of the invention, the container is selected from the group consisting of an eppendorf tube, a 96-well plate, a commercial cuvette or a cuvette adapted for use with a device comprising a contact image sensor module.

In further embodiments of the invention, the method may further comprise storing the container holding the lyophilised formulation away from light, oxygen and moisture.

In a fifth aspect of the invention, there is provided a kit of parts comprising:
(a) a creatinine assay formulation according to the formulation of the second aspect of the invention; and/or
(b) an albumin assay formulation and an albumin reference formulation according to the formulation of the third aspect of the invention.

In certain embodiments of the invention, in the kit of parts, each lyophilised formulation may be individually contained in an eppendorf tube, a cuvette, a cuvette adapted for use with a device comprising a contact image sensor module, or separate wells in a 96-well plate.

In certain embodiments, the formulations are stored away from light, oxygen and moisture.

In a sixth aspect of the invention, there is provided a computer-implemented method of generating a calibration curve for use in quantitatively determining the concentration of albumin in a urine sample, the method comprising the steps of:

obtaining, first absorbance data representing albumin-free sample absorbances and albumin-free reference absorbances for a plurality of albumin-free urine samples; wherein the albumin-free sample absorbances comprise absorbances for respective first portions of the albumin-free urine samples in the presence of an albumin-complexing reagent; and the albumin-free reference absorbances comprise absorbances for respective second portions of the albumin-free urine samples in the presence of the albumin-complexing reagent, and additionally in the presence of an albumin-denaturing reagent or a reagent that blocks the formation of a complex between albumin and the albumin-complexing reagent;

computationally fitting a functional relationship between the albumin-free sample absorbances and the albumin-free reference absorbances to obtain adjustment parameters;

obtaining second absorbance data representing sample absorbances and reference absorbances for a plurality of urine samples having known concentrations of albumin;

wherein the sample absorbances comprise absorbances for respective first portions of the urine samples in the presence of the albumin-complexing reagent; and the reference absorbances comprise absorbances for respective second portions of the urine samples in the presence of the albumin-complexing reagent, and additionally in the presence of the albumin-denaturing reagent or the reagent that blocks the formation of a complex between albumin and the albumin-complexing reagent;

adjusting the reference absorbances using the adjustment parameters, to thereby obtain adjusted reference absorbances; and computationally fitting a functional relationship between the sample absorbances, the adjusted reference absorbances and the known concentrations to obtain parameters of the calibration curve.

In an embodiment of the invention, the functional relationship between the albumin-free sample absorbances and the albumin-free reference absorbances is of the form $A_S^0 = a*A_R^0 + b$, where $A_S^0$ are the albumin-free sample absorbances, $A_R^0$ are the albumin-free reference absorbances, and a and b are the adjustment parameters.

In a further embodiment of the invention, the adjusted reference absorbances are calculated according to $a*A^*_R + b$, where $A^*_R$ are the reference absorbances.

In a still further embodiment of the invention, the functional relationship between the sample absorbances, the adjusted reference absorbances and the known concentrations is of the form $A^*_S - (a*A^*_R + b) = A*C^*_{Alb}$, where $A^*_S$ are the sample absorbances, $C^*_{Alb}$ are the known concentrations, and A is a parameter of the calibration curve.

DESCRIPTION OF THE ATTACHED DRAWINGS

FIG. 1: Sensing principle of albumin
FIG. 2: Sensing principle of creatinine
FIG. 3: Dry reagent preparation
FIG. 4: Cuvette cartridge and cuvette holder
FIG. 5: Sample introduction device
FIG. 6: Sample introduction structure
FIG. 7: Cuvette holder and optical module
FIG. 8: Assay method
FIGS. 9A-9C: BCG dry-reagent: Compensation of pH effect
FIG. 10A-10C: BCG dry-reagent: Compensation of temperature effect
FIG. 11: Calibration curve of BCG dry-reagent
FIG. 12: Calibration curve of BCG dry-reagent with real urine sample before data processing
FIG. 13: Graph of $A_S$ versus $A_R$
FIG. 14: Calibration curve of BCG dry-reagent with real urine sample after data processing
FIG. 15: Calibration curve of DNBA dry-reagent
FIG. 16: Functional diagram of a computer system.

DESCRIPTION OF INVENTION

It is desired to provide a simple and compact point-of-care urinalysis system using wet, or more particularly, dry reagents. In particular, the reagents may be suitable for use with a point-of-care analysis system that can simultaneously measure a number of analytical samples.

For example, such a system may comprise the use of a contact image sensor (CIS) module having a light emitting diode (LED) to emit light, the wavelength of the light is preconfigured to match the absorption wavelength of the reaction product of a urinalysis reagent and target analyte, an optical cuvette having the reflective surface at the far side of the cuvette from the CIS module, a freeze-dried urinalysis reagent being disposed in the optical cuvette, a urine distribution structure having reservoir to distribute sample urine into individual optical cuvette and having solution stopping structure to control the volume of distributed solution separately. Chronic Kidney Disease (CKD) can be diagnosed in its early stages by measuring microalbuminuria. Such tests can be performed by determining urine microalbuminuria and creatinine concentrations and their corresponding albumin/creatinine ratio (ACR).

While the tests used herein may be used to analyse a urine sample, the tests are also suitable for analysing samples from other sources (e.g. saliva, blood etc). As such, the term "urine microalbuminuria" may be replaced throughout the specification by the term "albumin".

In order to detect ACR, two different reagents are used for urine microalbuminuria and creatinine measurements, respectively. Bromcresol green (BCG) is used for urine microalbuminuria detection, while 3,5-dinitrobenzoic acid (DNBA) is used for urine creatinine detection.

Microalbuminuria present in a urine sample reacts with BCG to form a colored complex (FIG. 1). The intensity of the color, measured at a wavelength of 625 nm, is directly proportional to the microalbuminuria concentration in the urine sample.

For the microalbuminuria assay, two types of wet or, more particularly, dry reagents are prepared for sampling and referencing. The mixtures of the dry reagents (sampling and referencing) and the urine sample are measured concurrently by colorimetric assay. The sampling reagent is used to measure the intensity of the color obtained by the BCG-albumin complex. The referencing reagent is used to reduce or remove pH and temperature effects and interference by applying a protein denaturing method to the urine sample. That is, the microalbuminuria assay applies a protein denaturing method, where the dry reagent for referencing contains a surfactant to denature albumin, so that denatured albumin doesn't react with the BCG present in the referencing reagent.

Figure 2:
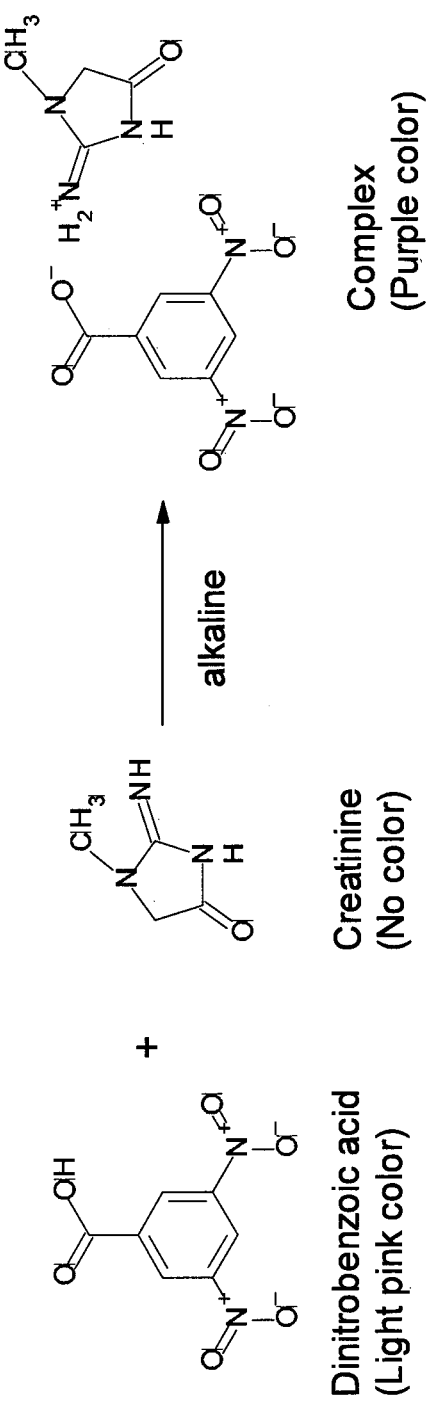

Creatinine present in a urine sample reacts with DNBA in alkaline medium to form a purple-red complex (FIG. 2). The rate of complex formation at wavelength of 525 nm is directly proportional to the concentration of creatinine in the urine sample. Alternatively, DNBA may be replaced by picric acid.

The creatinine assay only uses a sampling reagent for measuring creatinine. The creatinine sampling reagent applies a buffer addition method to minimise the interference from urine pH, while the temperature effect is compensated by a temperature factor in the calibration curve and the urine background effect is eliminated by measuring the rate of complex formation. Current, devices are tailored so as to operate within the reaction parameter of conventional formulations. This may result in a more complicated automated device, as differing sensors may need to be used to analyse the reaction products of the different reagents used to detect analytes in urine (e.g. colourimetric analysis).

As described in more detail below, it is important to control the kinetics of the interaction between DNBA and creatinine. If the reaction between DNBA and creatinine is too fast or too slow for the device being used, then the device will not be able to provide an accurate analysis. In addition, as the mixture of DNBA dry-reagent and urine sample has a tendency to form bubbles, the analysis may not be accurate due to light scattering. The formulations disclosed herein has been formulated in order to overcome such problems associated with the reagent and the analysis of the sample.

Dry Reagent for Creatinine Assay

A buffer addition method is applied to the DNBA dry-reagent to remove the effect of urine pH. DNBA reacts with creatinine under alkaline conditions, and a purple-colored complex is generated. The sampling reagent contains DNBA, a strong base, a buffer, a bulking agent, an anionic surfactant and a cationic surfactant. The specific chemicals used can be chosen from the list below (Table A), and the concentration of each chemical can be within the specified range.

TABLE A

| Chemical Category | Range of Concentration Creatinine-Sampling reagent |
| --- | --- |
| Strong base | 40-80 g/L |
| Buffer | 50-250 g/L |
| Bulking agent | 1-40 wt % |
|  | (10-400 g/L) |
| Anionic surfactant | 0.1-10 g/L |
| Cationic surfactant | 0.1-10 g/L |
| DNBA | 1-5 g/L |

Chemical List for Creatinine Assay
1) Strong base; NaOH, KOH.
2) Buffer; $K_2HPO_4$, $Na_2HPO_4$, Borate.
3) Bulking agent; Sugar (e.g. mannitol, lactose, trehalose).
4) Anionic surfactant; especially anionic sulphated/sulphonated surfactant; Sodium dodecyl sulfate (SDS), Polystyrene sulfonates (PSS), linear alkylbenzene sulfonate (LAS), secondary alcohol sulfonate, alcohol olefin sulfonate, alcohol sulfate.
5) Cationic surfactant; Cetylpyridinium chloride (CPC), Benzalkonium chloride (BAC), Benzethonium chloride (BZT), Dimethyldioctadecyl-ammonium chloride, Cetrimonium bromide, Dioctadecyldimethyl-ammonium bromide (DODAB), Hexadecyltrimethylammonium bromide (CTAB).

Without wishing to be bound by theory, it is suspected that the addition of a buffer to the strong base results in the kinetic modulation of the chemical reaction between DNBA or picric acid and creatinine. As will be appreciated, the ratio of buffer and sodium hydroxide may be selected to suit the analytical device. This enables the device to produce a more accurate reading. For example, the concentration ratio (in Molar) of the buffer:strong base may be from 0.5:1 to 3.2:1, such as from 0.8:1 to 2.5:1 (e.g. from 1.5:1 to 2.5:1), such as from 1:1 to 1.5:1 (e.g. 1.25:1). For example, when used with the device described in FIGS. 4 to 7 of the current application, a buffer:strong base ratio of less than 0.5:1 may result in the complex formation becoming too quick to accurately measure the rate of its formation.

In addition, without wishing to be bound by theory; it is believed that the addition of surfactants helps to reduce the formation of bubbles on the optical cuvette wall in the reaction mixture, thereby reducing scattering and increasing accuracy. In particular, it has been found that the use of a cationic surfactant that includes a quarternary ammonium moiety is useful in controlling the formation of bubbles when used in combination with an anionic surfactant as a solvation assistant. This is because the quarternary ammonium surfactant is not able to dissolve in sufficient quantity in the buffered solution without a solvation aid (e.g. an anionic surfactant), while the anionic surfactant does not affect bubble formation when used alone. Therefore, in order to control bubble formation, it is useful to use a specific ratio of anionic and cationic surfactants in the creatinine assay reagent. The ratio of the cationic surfactant:anionic surfactant may be from 1:2 to 1:10, such as from 1:3 to 1:7 or, more particularly, 1:5.

Dry Reagent for Microalbuminuria Assay

A protein denaturing method is applied for the BCG dry-reagent to remove the interference from the urine components, such as urine pH, sample temperature and urine background. Albumin reacts with BCG and the color changes, but denatured albumin does not react with BCG and the color remains the same. The $1^{st}$ reagent is for sampling and the $2^{nd}$ reagent is for referencing. Both reagents contain the same concentrations of BCG, Strong base, buffer, non-ionic surfactant and preservative. However, only the $2^{nd}$ reagent contains an anionic surfactant to denature albumin in the reference sample. The chemicals can be chosen from the list provided below (Table B), and the concentrations can be within the specified range.

TABLE B

| | Range of Concentration | |
| --- | --- | --- |
| Chemical Category | Albumin-Sampling reagent | Albumin-Referencing reagent |
| BCG | 0.1-1.5 g/L | 0.1-1.5 g/L |
| Strong base | 10-50 g/L | 10-50 g/L |
| Buffer | 50-250 g/L | 50-250 g/L |
| Non-ionic surfactant 2 | 1-20 wt % | 1-20 wt % |
| | (10-200 g/L) | (10-200 g/L) |
| Non-ionic surfactant 1 | 1-20 g/L | 1-20 g/L |
| Preservative | 0.1-3 g/L | 0.1-3 g/L |
| Anionic surfactant | 0 w % | 0.1-5 w % |
| | | (1-50 g/L) |

Chemical List for Albumin Assay
1) Strong base; NaOH, KOH.
2) Buffer; ACES (N-(1-Acetamido)-2-aminoethanesulfonic acid), Acetate (Sodium acetate), ADA (N-(2-Acetamido)-iminodiacetic acid), AMP (2-Amino-2-methyl-1-propanol), AMPD (2-Amino-2-methyl-1,3-propanediol), AMPSO (N-(1,1-Dimethyl-2-hydroxyethyl)-3-amino-2-hydroxypropanesulfonic acid), BES (N,N-Bis-(2-hydroxyethyl)-2-aminoethanesulfonic acid), Bicarbonate (Sodium hydrogen carbonate), Bicine (N,N-Bis-(2-hydroxyethyl)-glycine), Bis-Tris (Bis-(2-hydroxyethyl)-imino-tris-(hydroxymethyl)-methane), Bis-Tris-Propane (1,3-Bis-[tris-(hydroxymethyl)-methylamino]-propane), CAPS (3-Cyclohexylamino)-1-propanesulfonic acid), CAPSO (3-(Cyclohexylamino)-2-hydroxy-1-propanesulfonic acid), CHES (2-(N-Cyclohexylamine)-ethanesulfonic acid), Citrate (tri-Sodium citrate), DIPSO (N,N-Bis-(2-hydroxyethyl)-3-amino-2-hydroxypropanesulfonic acid), HEPES (4-(2-Hydroxyethyl)-pipera-zine-1-ethanesulfonic acid), HEPPS (4-(2-Hydroxyethyl)-piperazine-1-propanesulfonic acid), HEPPSO (4-(2-Hydroxyethyl)-piperazine-1(2-hydroxy)-propane-sulfonic acid), MES (2-Morpholinoethanesulfonic acid), MOPS (3-Morpholinopropanesulfonic acid), MOPSO (3-Morpholino-2-hydroxypropanesulfonic acid), PIPES (Piperazine-1,4-bis-(2-ethanesulfonic acid)), POPSO (Piperazine-1,4-bis-(2-hydroxy-propanesulfonicacid)), TAPS (N-[Tris-(hydroxymethyl)-methyl]-3-aminopropanesulfonic acid), TAPSO (N-[Tris-(hydroxymethyl)-methyl]-3-amino-2-hydroxypropanesulfonic acid), TES (N-[Tris-(hydroxymethyl)-methyl]-2-aminoethanesulfonic acid), Tricine (N-[Tris-(hydroxymethyl)-methyl]-glycine), Tris (Tris-(hydroxy-methyl)-aminomethane), Succinic Acid.
3) Non-ionic surfactant; Poly(propylene glycol) (PPG), Polyethylene glycol hexadecyl ether (Brij), Triton X-100, Tween, Zonyl® FSN fluorosurfactant, ALKA-NOL® 6112 surfactant, Polyethylene Glycol (PEG).
4) Preservative; Sugar, sorbic acid, benzoic acid, calcium propionate, sodium nitrite, sodium azide, sulfites, disodium EDTA, Antioxidants.
5) Anionic surfactant; Sodium dodecyl sulfate (SDS), Polystyrene sulfonates (PSS), linear alkylbenzene sulfonate, (LAS), secondary alcohol sulfonate, alcohol olefin sulfonate, alcohol sulfate.

Figure 3:
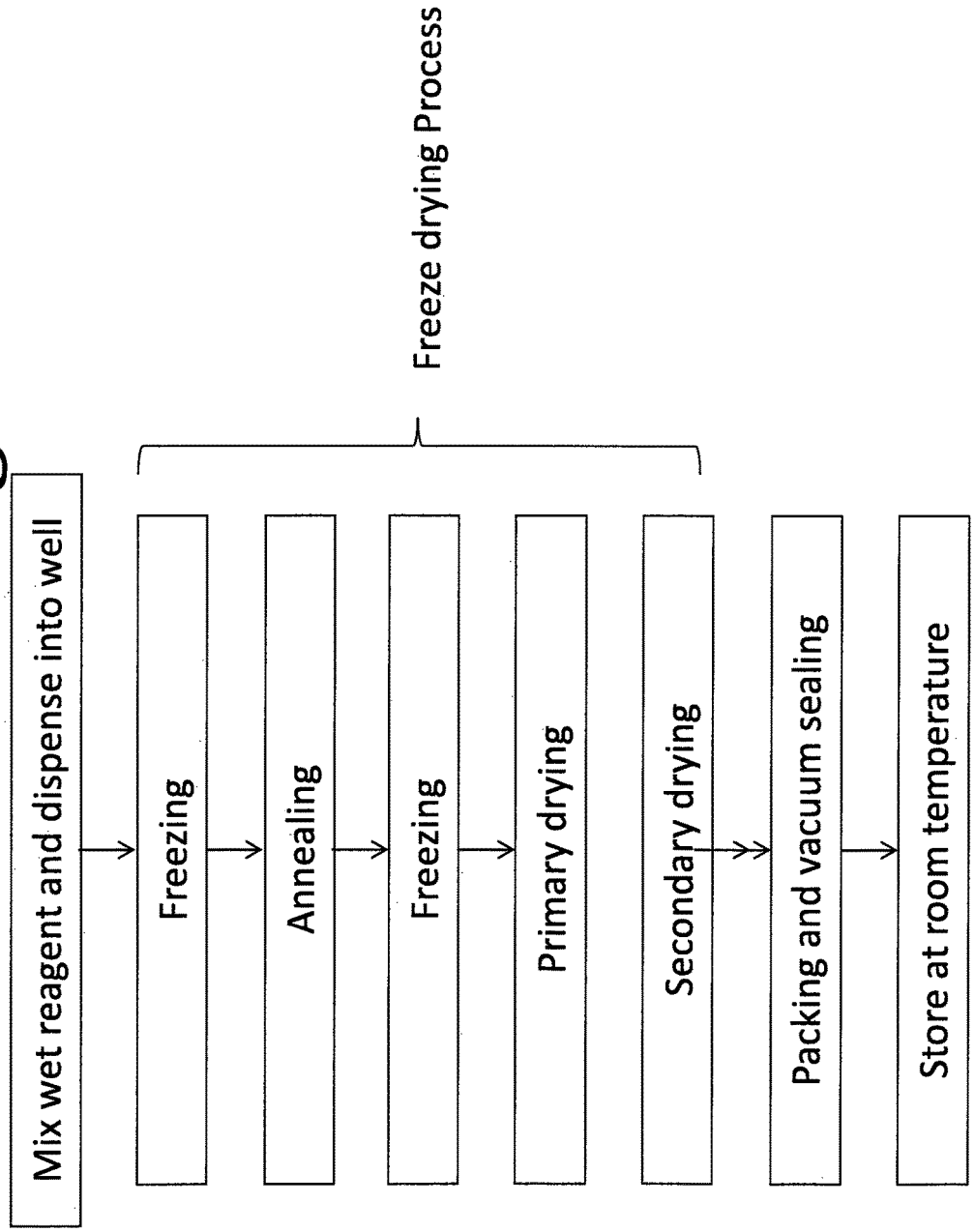

Method of Preparing Dry Reagent (FIG. 3)

Figure 4:
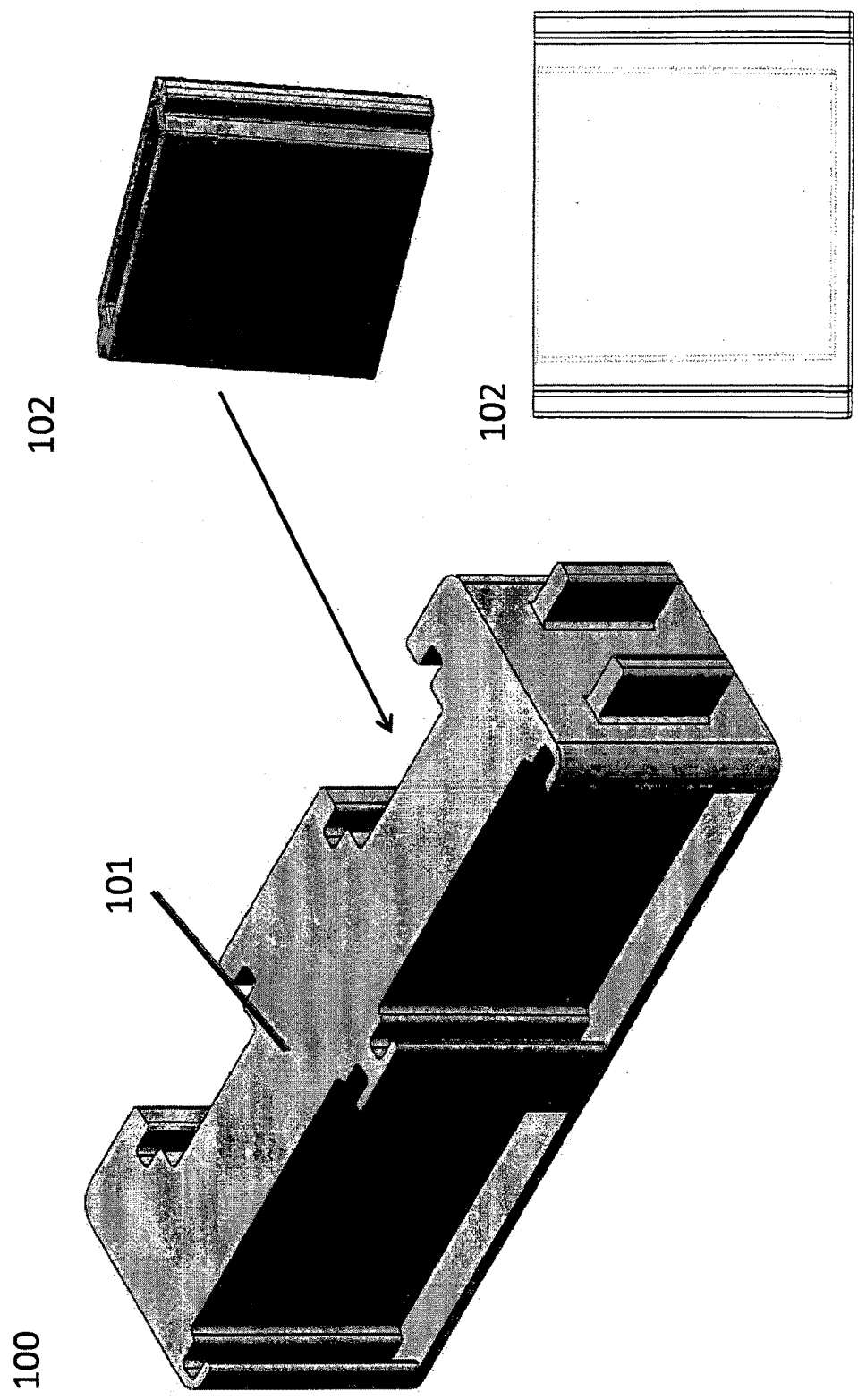

The prescribed chemical components are mixed and filtered through a 0.45 µm cellulose acetate filter disk. The filtered mixture is dispensed into an appropriate sample well by pipette or dispenser. The sample well can be an eppendorf tube, a 96 well plate, a commercial cuvette, or any other equivalent reagent holder. For example, the sample well may be a cuvette cartridge (102) as depicted in FIG. 4. The sample well is inserted into a freeze-dryer and freeze-dried under a specific profile, which consists of freezing, annealing, freezing, primary drying and secondary drying processed. The freeze-drying process can be performed under moisture-less conditions to avoid contact with moisture.

The use of other reagent holders may require optimization of the primary drying duration (e.g. extension of duration).

An example of the freeze-drying profile and the range of parameters is provided in the table below. These conditions may be particularly suited to the cuvette cartridge depicted in FIG. 4.

| Freeze Drying Process | Temp [° C.] | Duration [hr] | Vacuum [mTorr] |
|---|---|---|---|
| Freezing | −20 to −80 | 0.5 to 5 | N/A |
| Annealing | −10 to −30 | 1 to 5 | N/A |
| Freezing | −20 to −80 | 0.5 to 5 | N/A |
| Primary drying | −10 to −30 | 5 to 50 | 50-300 |
| Secondary drying | 0 to 60 | 1 to 20 | 50-300 |

Packaging

The dried reagent should be stored in the dark and in dry conditions to prevent light, moisture and oxygen exposure. The dried reagent can be packed into moisture barrier bags and vacuum sealed in a glove box (i.e. under an inert atmosphere). If necessary, a desiccant or an antioxidant can be inserted into the package.

Cuvette Cartridge, Introduction Device and Assay Method

A cuvette cartridge system and sample introduction device can be utilized with the dry reagent (e.g. as depicted in FIGS. 4 to 7). The width of the cartridge may be calculated based on the path length of each analyte. Volume can be the same in each cuvette cartridge (102) when the assay is for multiple analytes. For example, the volume can be 0.5 mL to 5 mL, preferably 1 mL. For example, if the volume is 1 mL, then the cuvette width can be 5 mm for the Albumin assay, and 2 mm for the creatinine assay. The cuvette cartridge (102) can be made of transparent material, such as PMMA (Poly-methyl methacrylate, PC (Polycarbonate), COC (Cyclic Olefin Copolymer). To block stray light, the color may be black.

Liquid reagent is dispensed into a cuvette cartridge (102) by dispenser (e.g. a Musashi Dispenser), and freeze-dried by a Freeze-dryer (VirTis AdVantage Plus Freeze-dryer). For example, using the method of preparing and storing the dry reagent used above. It will be appreciated that the reagent may be used in "wet" form, that is, without freeze-drying. The cuvette cartridge (102) is transferred into a cuvette holder (100; FIG. 4).

Figure 7:
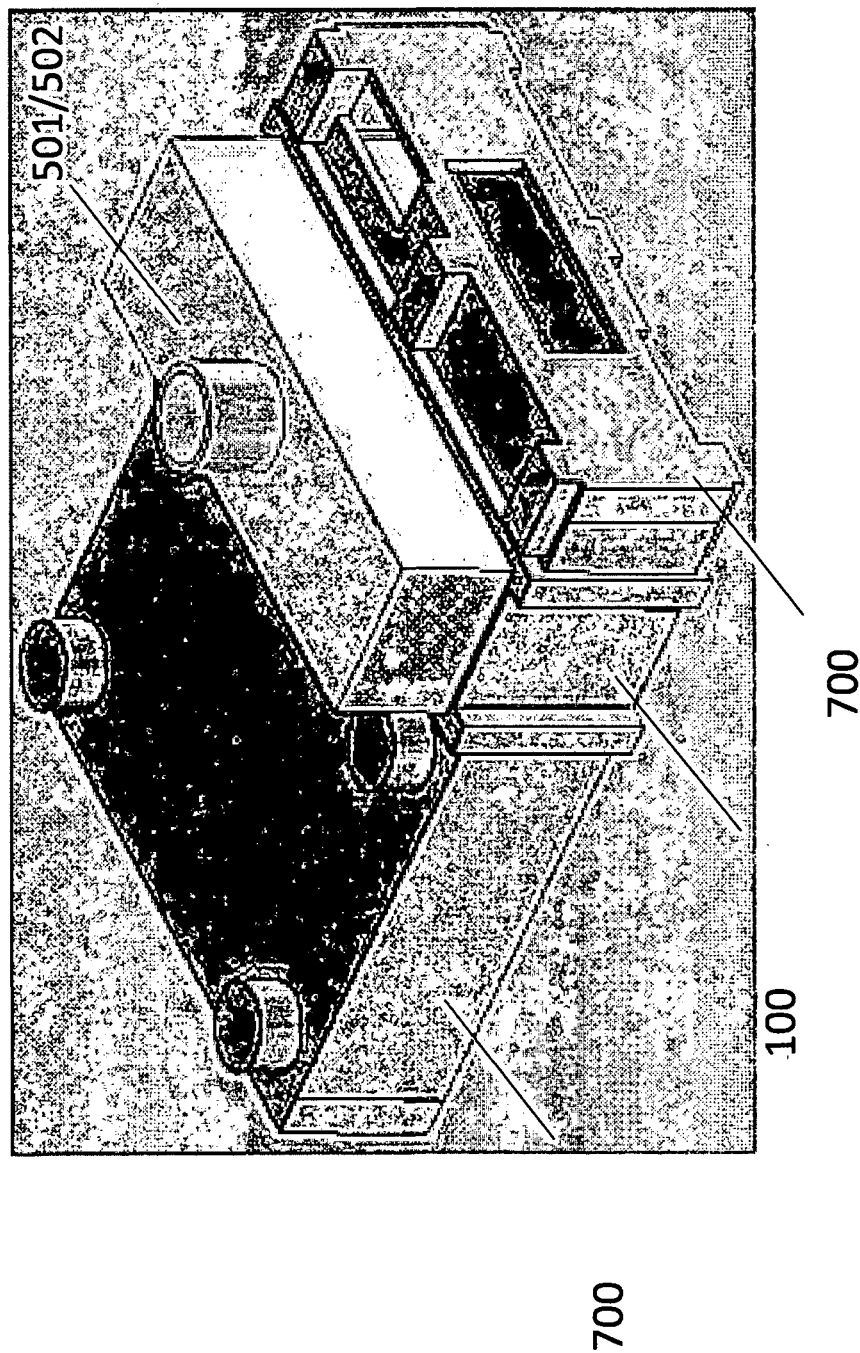

As shown in FIG. 4, the cuvette holder (100) can hold 4 cuvette cartridges (102). For example 4 cuvettes can be arranged in 2 lines separated by a light blocking structure (101). 2 cuvette cartridges (102) can be used for one analyte, and the other 2 cuvette cartridges can be used for the other analyte. As shown in FIG. 7, two optical modules (700) can be arranged to each side of the cuvette holder (100). It will be appreciated that the cuvette holder (100) also serves to maintain the distance between the cuvette (102) and the light module (700), so that a certain path length is maintained during sample measurement.

Figure 5:
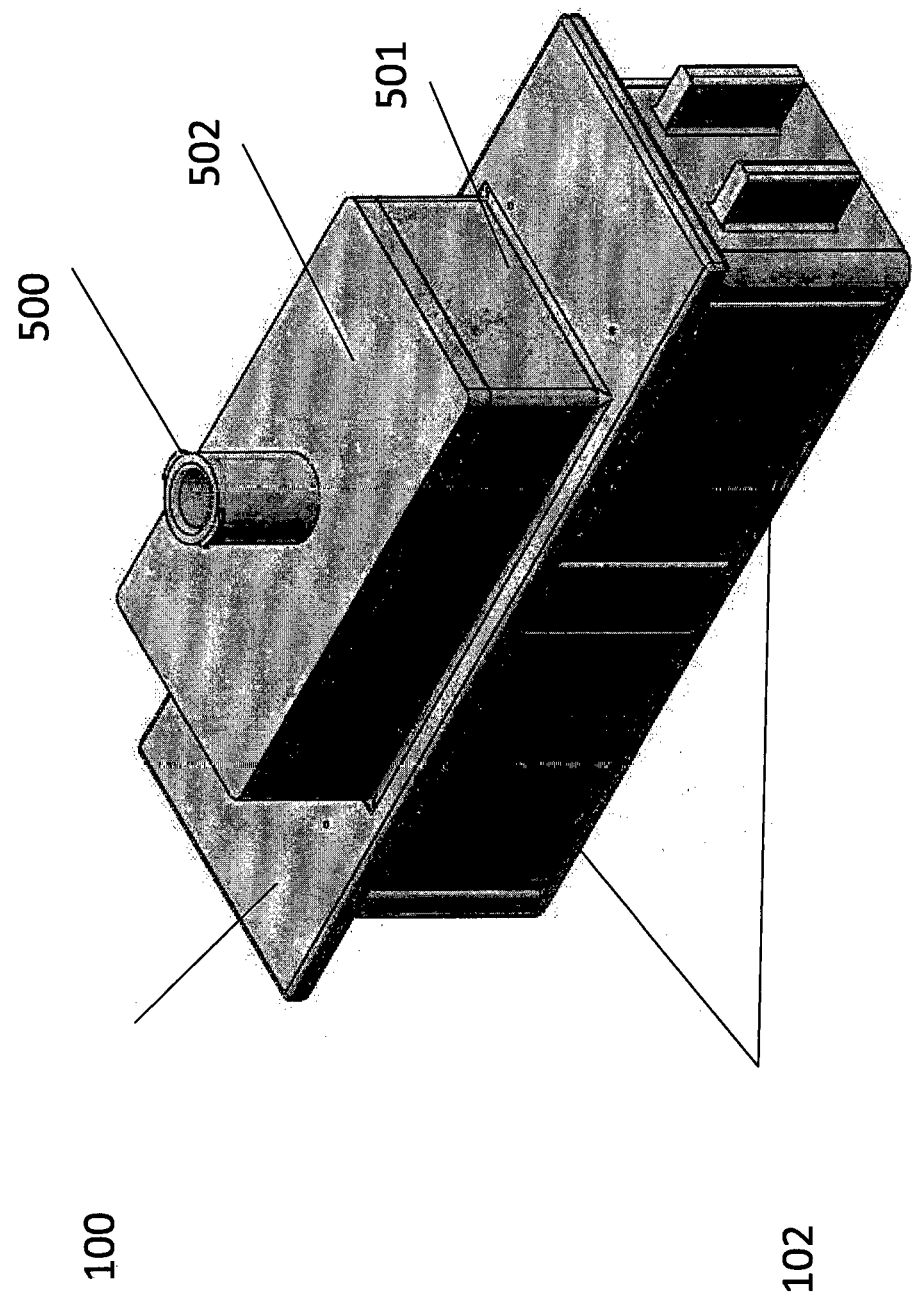
Figure 6:
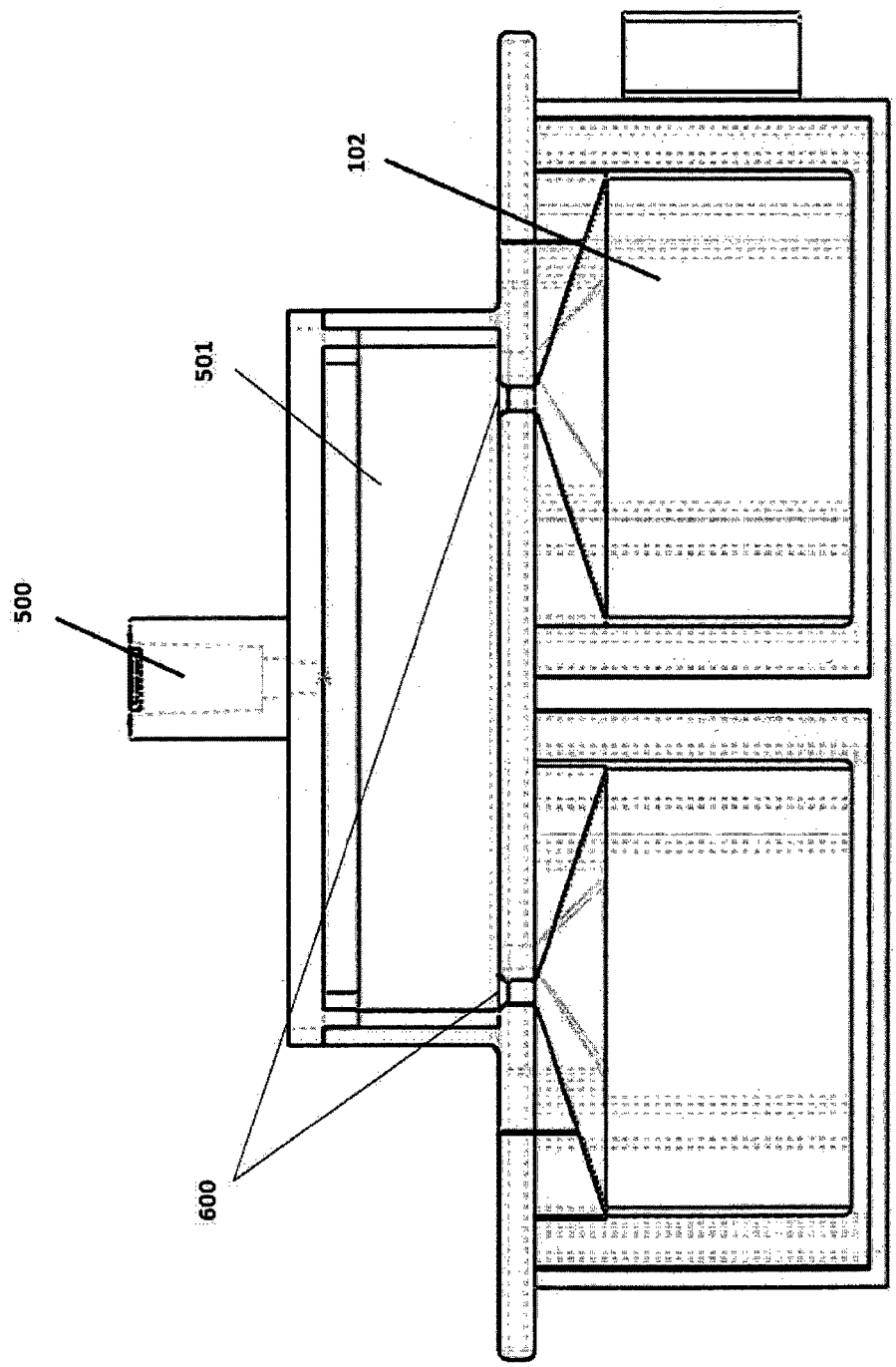
Figure 8:
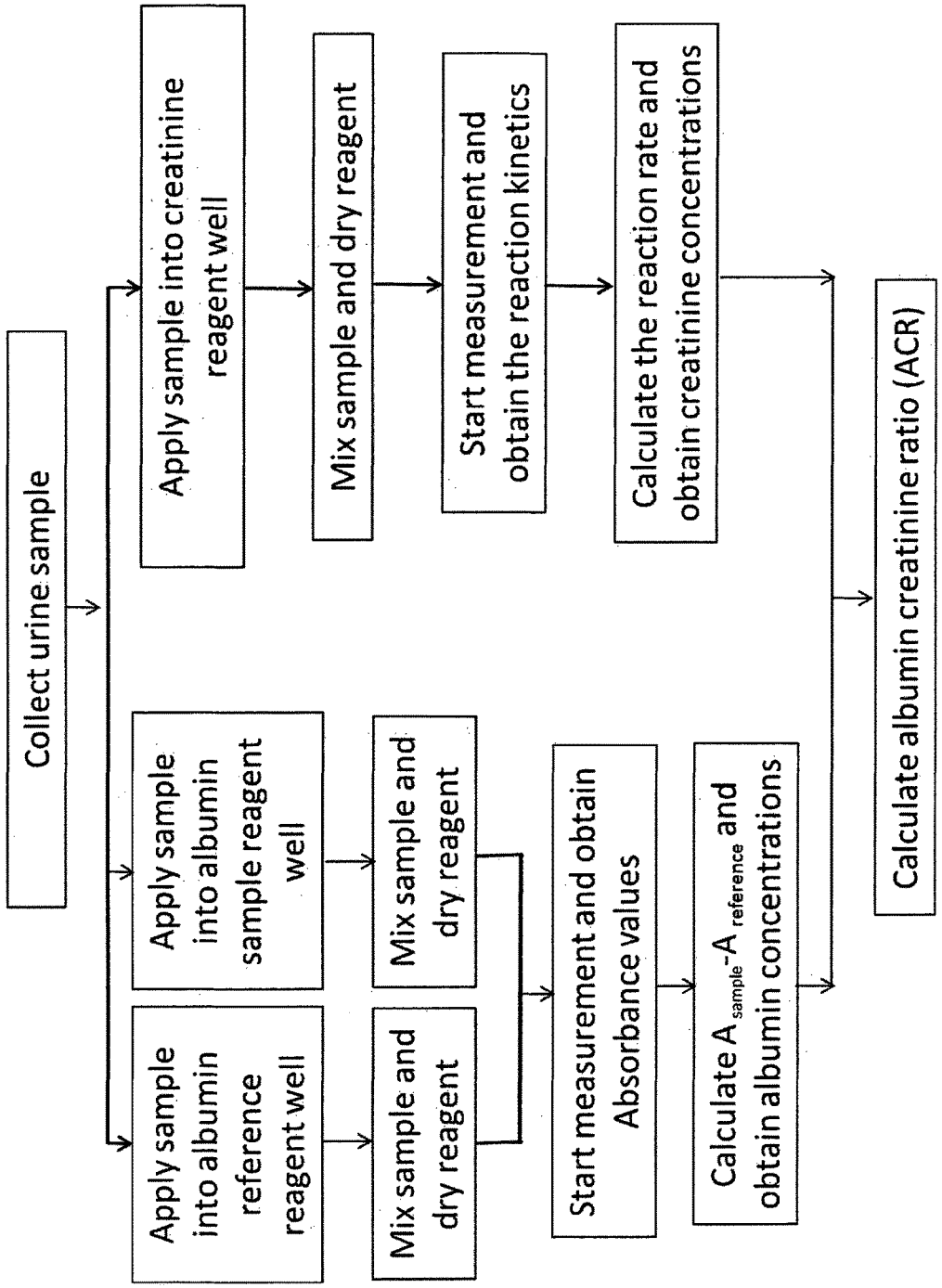

Urine is collected from a subject into a collection cup, sucked up into a syringe and introduced into a sample well (501; FIG. 5) through a sample introduction port (500) in a sample well cover (502). Urine is dispensed into each cuvette (102) through a sample introduction hole (600; FIG. 6). Urine and dry reagent are mixed in the cuvette cartridge by shaking, magnetic stirring, vibration, sonication, or in any other equivalent way. Optical measurement is performed using one or more optical modules (700; FIG. 7). As shown in FIG. 8, the absorbance value is measured for each cuvette, and, where necessary, the difference between the sample and reference is calculated. By utilizing a calibration curve which has been prepared beforehand, the analyte concentration can be calculated, and the albumin to creatinine ratio can be calculated thereafter.

Figure 9:
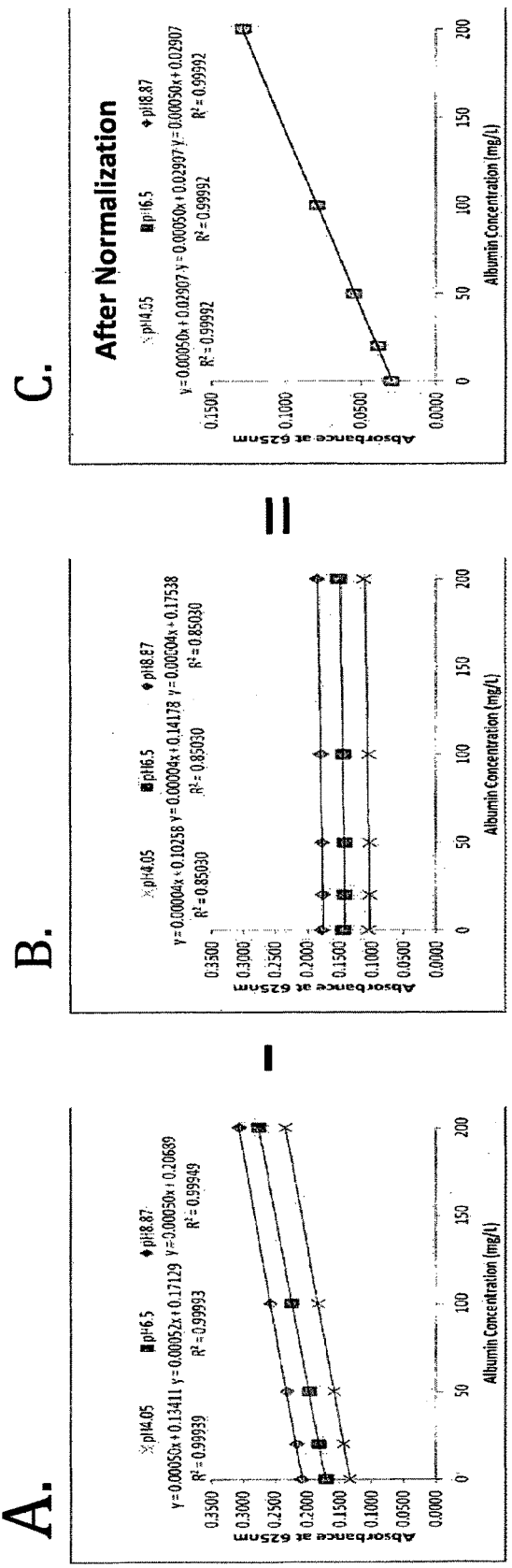
Figure 11:
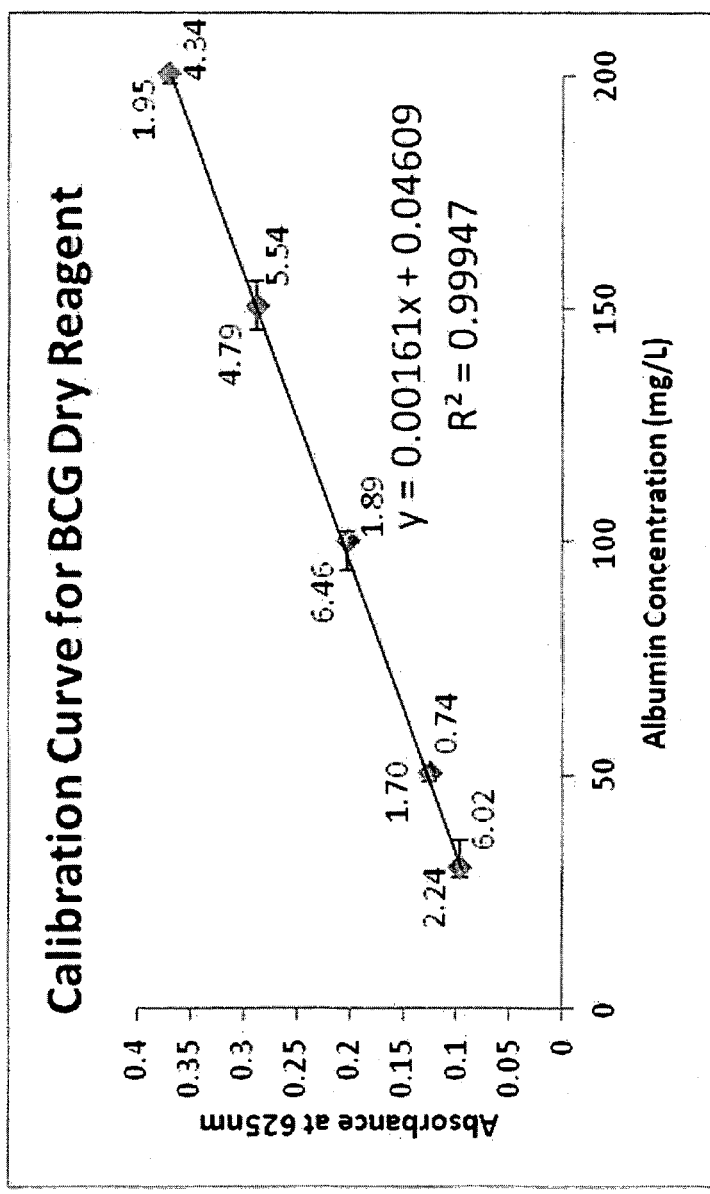

FIGS. 9-11 show a calibration curve for the microalbuminuria assay based upon synthetic standards (e.g. a synthetic urine matrix). These albumin standards are prepared with artificial or pooled urine and a certain concentration of albumin. FIGS. 9A and 10A use the sampling reagent, FIGS. 9B and 10B use the referencing reagent, FIGS. 9C, 10C and 11 show the calibration curve, which results from the difference between the sampling reagent and referencing reagent when contacted with, the standards. Table 1 shows the results obtained before normalization of the results in FIGS. 9A-9C for pH variations, while Table 2 shows the results obtained after normalization using equation (1) below. Table 3 shows the results before normalization found in FIGS. 10A-10C, while. Table 4 provides the data normalized to compensate for temperature effects.

TABLE 1

Estimated [Albumin] in mg/L

| [Albumin] | pH 5.08 | pH 6.65 | pH 8.07 |
|---|---|---|---|
| 0 | −55.81 | 3.93 | 54.19 |
| 20 | −39.66 | 20.00 | 77.35 |
| 50 | −8.89 | 49.91 | 104.96 |
| 100 | 32.82 | 100.77 | 151.79 |
| 200 | 139.15 | 200.43 | 241.71 |

TABLE 2

Estimated [Albumin] in mg/L

| [Albumin] | pH 5.08 | pH 6.65 | pH 8.07 |
|---|---|---|---|
| 0 | 0.51 | −2.73 | −0.32 |
| 20 | 24.12 | 19.21 | 23.94 |
| 50 | 49.40 | 50.14 | 55.97 |
| 100 | 94.49 | 100.51 | 101.62 |
| 200 | 196.62 | 198.94 | 201.81 |

TABLE 3

| [Alb] | 25° C. | 28° C. | 31° C. | 34° C. |
|---|---|---|---|---|
| 0 | −2.20 | 6.83 | 17.56 | 36.10 |
| 20 | 18.78 | 27.32 | 37.32 | 55.61 |
| 50 | 48.78 | 58.29 | 67.80 | 85.85 |
| 100 | 103.90 | 110.98 | 120.00 | 137.07 |
| 200 | 198.29 | 204.63 | 213.17 | 229.51 |

TABLE 4

Figure 12:
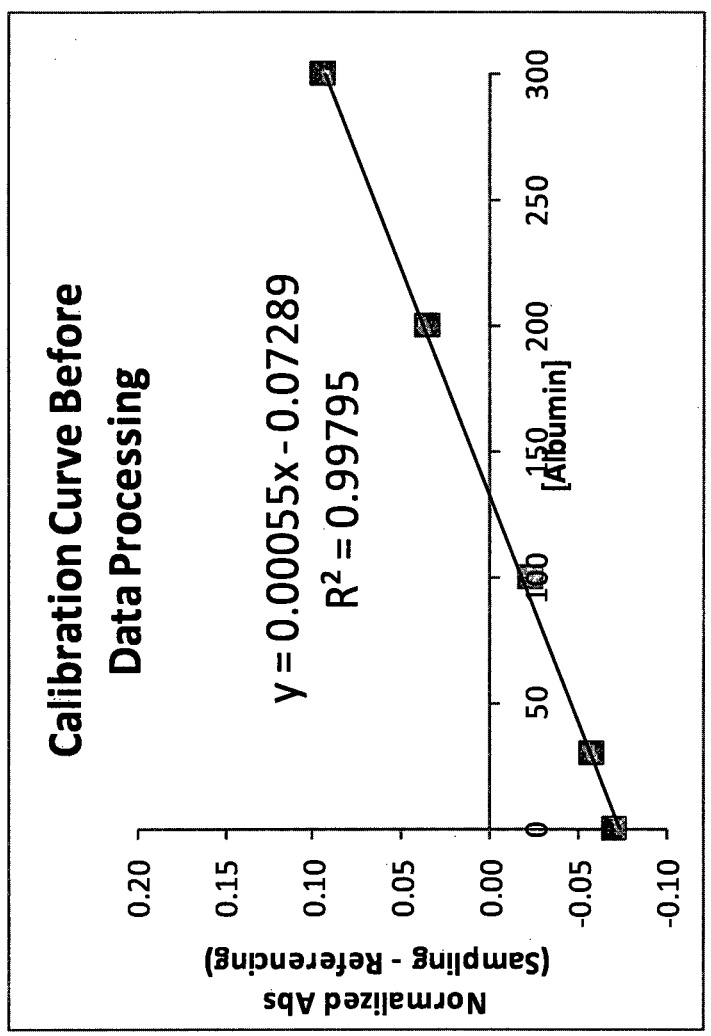

| [Alb] | 25° C. | 28° C. | 31° C. | 34° C. |
|---|---|---|---|---|
| 0 | −1.05 | −1.05 | 1.77 | 5.36 |
| 20 | 19.46 | 17.41 | 19.72 | 19.46 |
| 50 | 46.64 | 47.41 | 49.72 | 53.31 |
| 100 | 106.38 | 102.54 | 104.33 | 106.64 |
| 200 | 198.18 | 195.36 | 196.13 | 197.15 |

$$A_S - A_R = A^* C_{Alb} B \quad (1)$$

Where $A_S$ refers to the sampling reagent, $A_R$ refers to the referencing reagent, $C_{Alb}$ refers to the concentration of albumin and A and B are constants. While the resulting calibration curve was found to be accurate for subjects with medium to high levels of albumin (e.g. 30-300 mg/L), it was found that the results obtained for low levels of albumin (e.g. 0-30 mg/L) could vary significantly. These results are depicted in FIG. 12 and in Table 5 (i.e. the unspiked urine samples should have an average concentration of around 0 mg/L). It is believed that this inaccuracy is caused by a urine matrix side-effect, which results in greater variation at lower concentrations.

TABLE 5

| | Quantified [Albumin] | |
|---|---|---|
| Vol. # | Un-spiked | Spiked 100 mg/L |
| 1 | 14 | 102 |
| 2 | 18 | 116 |
| 3 | 8 | 104 |
| 4 | 5 | 101 |
| 5 | 3 | 99 |
| 6 | 6 | 104 |
| 7 | 14 | 107 |
| 8 | 15 | 105 |
| 9 | 8 | 105 |
| 10 | −1 | 101 |
| Average | 9 | 104 |
| Stdev | 6.20 | 4.77 |

In order to improve the accuracy of the assay at low albumin concentrations in real human samples, it was necessary to conduct further processing, as described below.

Original calibration curve:

$$A_S - A_R = A^* C_{Alb} + B$$

For blank sample (normal urine; 0 mg/L albumin):

$$A_S^o - A_R^o = A^* C_{Alb} + B \quad (2)$$

For spiked sample:

$$A^*_S - A^*_R = A^* C^*_{Alb} + B \quad (3)$$

If the result of the spiked sample is normalized with the blank sample (i.e. equation (3) minus equation (2)), equation (4) is obtained.

$$(A^*_S - A_S^o) - (A^*_R - A_R^o) = A^* (C^*_{Alb} - C_{Alb}^o) \quad (4)$$

Assuming that $A^*_R = A_R^o$, i.e. the absorbance of the referencing reagent is the same for the Blank and Spiked samples, then equation (4) can be rewritten as equation (5):

$$A^*_S - A_S^o = A^* (C^*_{Alb} - C_{Alb}^o) \quad (5)$$

Figure 13:
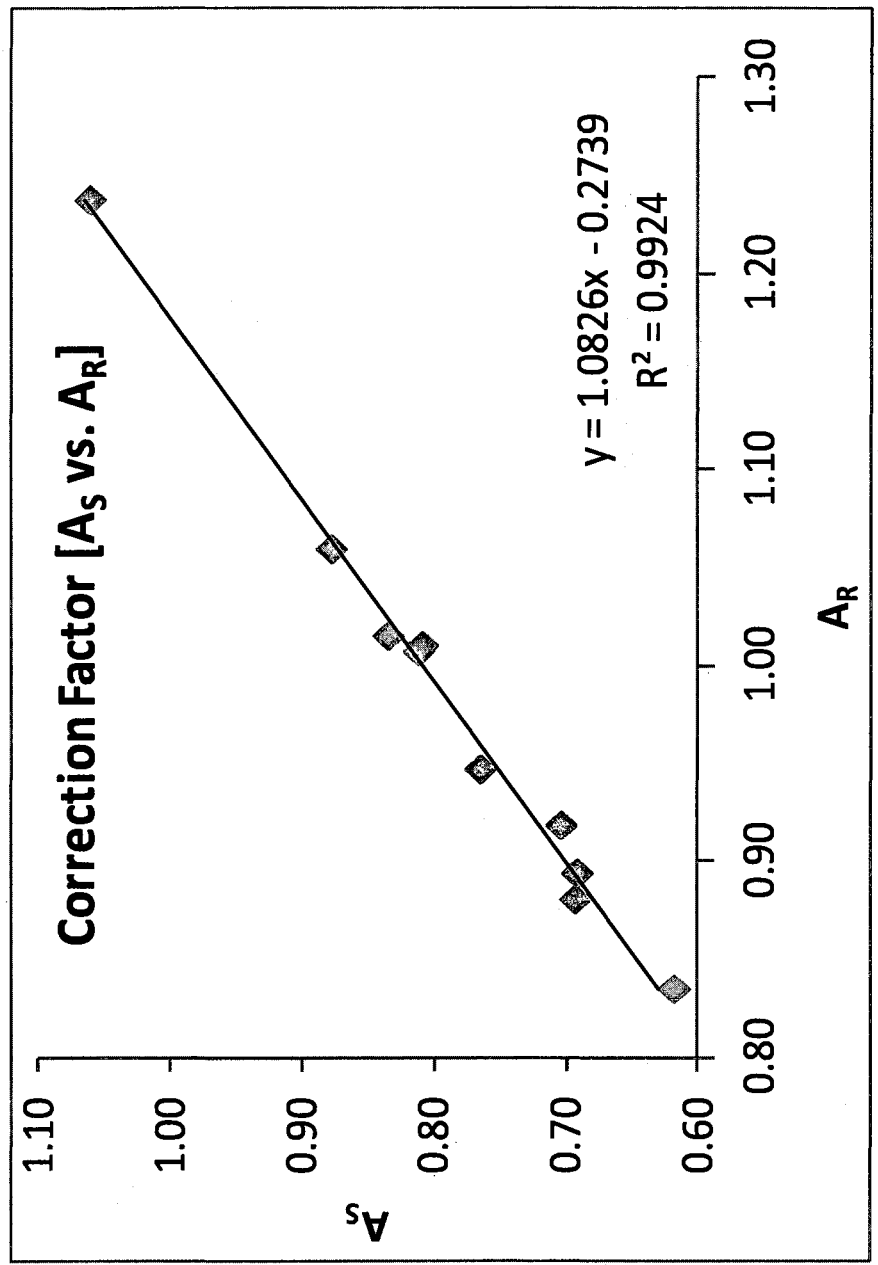

While it is possible to measure $A^*_S$ and $A^*_R$, $A_S^o$ is an unknown. However, a strong correlation is found between $A_S^o$ and $A_R^o$, which counters the urine matrix effect in different real urine samples as shown in FIG. 13 and equation (6).

$$A_S^o = a^* A_R^o + b = a^* A^*_R + b \quad (6)$$

By substituting equation (6) into equation (5), a new calibration curve for the albumin assay can be obtained using equation (7) (wherein $C^*_{Alb}$ is taken as being 0 mg/L).

$$A^*_S - (a^* A^*_R + b) = A^* C_{Alb} \quad (7)$$

Figure 14:
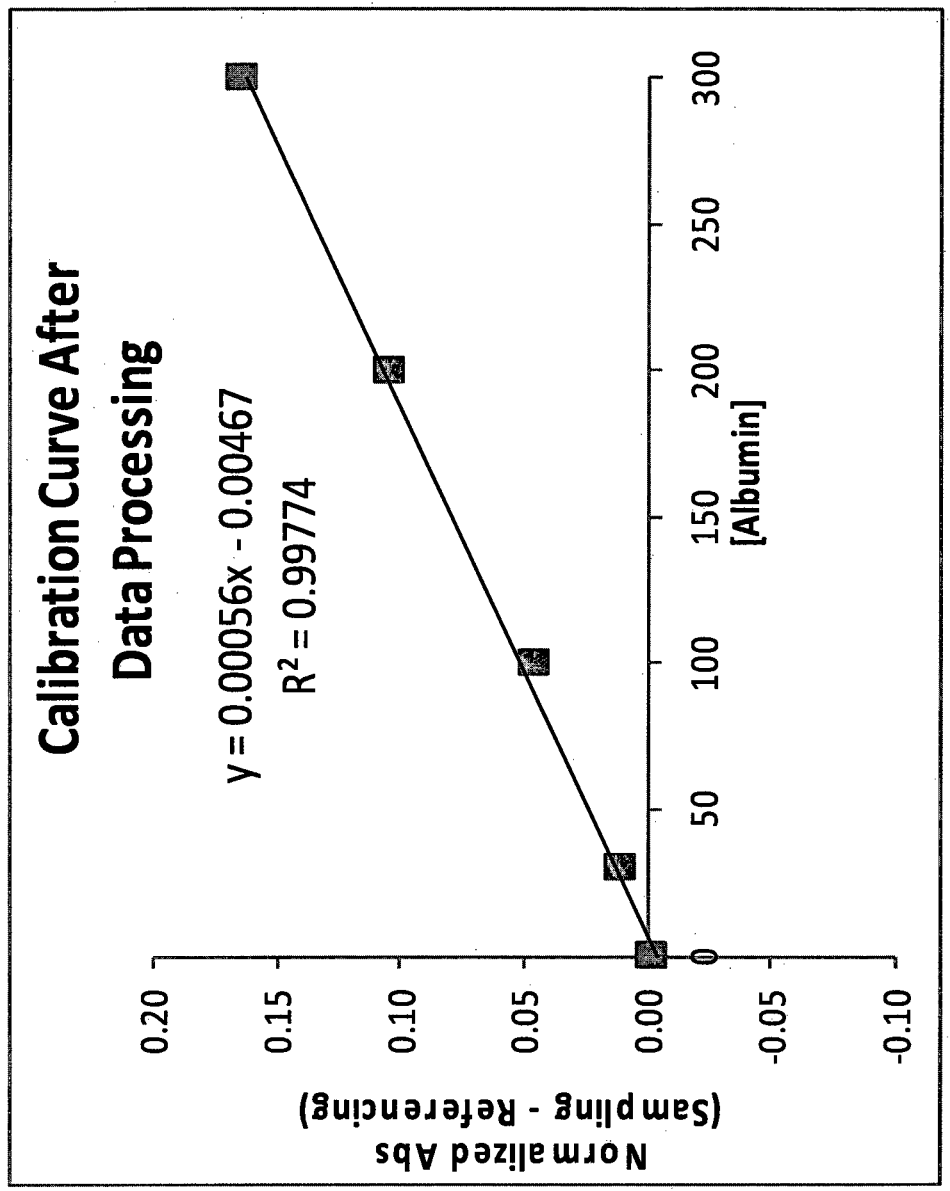

The normalised curve calibration curve of FIG. 14 is more accurate across the concentration range, and especially at low concentrations of albumin. This is illustrated in Table 6.

TABLE 6

| | Quantified [Albumin] | |
|---|---|---|
| Vol. # | Un-spiked | Spiked 100 mg/L |
| 1 | −1 | 89 |
| 2 | 9 | 110 |
| 3 | 1 | 100 |
| 4 | 1 | 100 |
| 5 | −6 | 93 |
| 6 | 0 | 101 |
| 7 | −2 | 95 |
| 8 | 2 | 94 |

TABLE 6-continued

| | Quantified [Albumin] | |
|---|---|---|
| Vol. # | Un-spiked | Spiked 100 mg/L |
| 9 | 2 | 102 |
| 10 | −8 | 96 |
| Average | 0 | 98 |
| Stdev | 4.69 | 5.81 |

Figure 16:
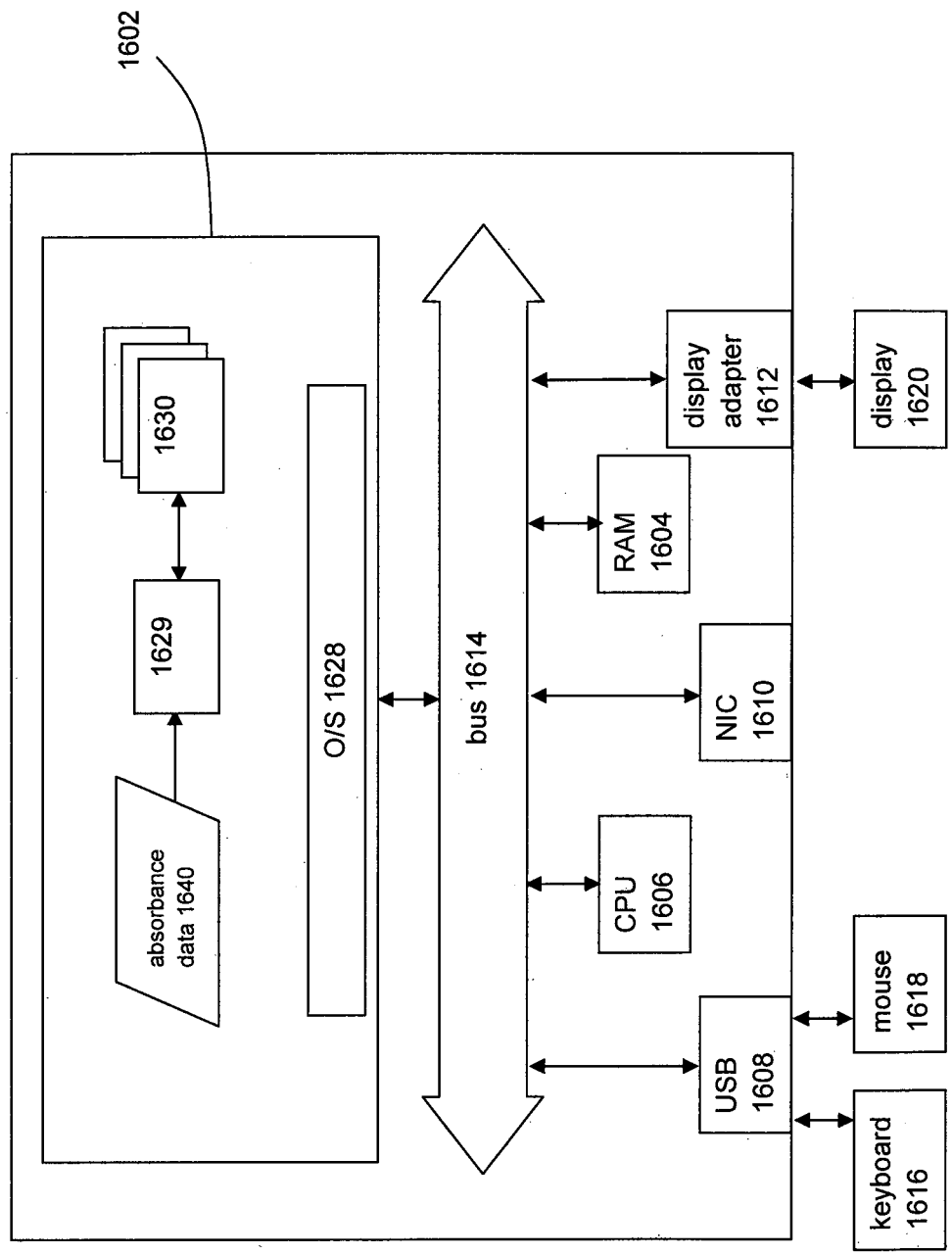

The above-described calibration process may be implemented as one or more software modules executed by a standard computer system such as an Intel IA-32 based personal computer system, as shown in FIG. 16. However, it will be apparent to those skilled in the art that at least parts of the calibration process could alternatively be implemented in part or entirely in the form of one or more dedicated hardware components, such as application-specific integrated circuits (ASICs), and/or field programmable gate arrays (FPGAs), for example.

As shown in FIG. 16, a system 1600 for generating a calibration curve for use in quantitatively determining the concentration of albumin in a urine sample executes a calibration process, as described above, which is implemented as one or more software components 1630 stored on non-volatile (e.g., hard disk, solid-state drive, or flash memory) storage 1602 associated with a standard computer system. The system 1600 includes standard computer components, including random access memory (RAM) 1604, at least one processor 1606, and external interfaces 1608, 1610, 1612, all interconnected by a bus 1614.

The external interfaces include universal serial bus (USB) interfaces 1608, at least one of which is connected to a keyboard 1616 and a pointing device such as a mouse 1618, a network interface connector (NIC) 1610 which can be used to connect the system 1600 to a communications network such as the Internet, and a display adapter 1612, which is connected to a display device such as an LCD panel display 1620. The system 100 also includes a number of standard software components, including an operating system 1628 such as Linux or Microsoft Windows, and a statistical software package 1629 such as Matlab or R.

The system 1600 stores, on non-volatile storage 1602, absorbance data 1640, which comprise first absorbance data representing the albumin-free sample and reference absorbances $A_S^\circ$ and $A_R^\circ$, and second absorbance data representing the spike-in sample and reference absorbances $A*_S$ and $A*_R$. The absorbance data 1640 may be stored from previous experiments, or may be obtained in real time from absorbance measurements carried out on albumin-free and spike-in samples using optical modules 700 and communicated to system 1600 via NIC 1610, for example.

The software components 1630 may comprise a first fitting component configured to computationally fit, using statistical software package 1629 for example, the functional relationship described in Eq. (6) between the albumin-free sample absorbances and the albumin-free reference absorbances to obtain adjustment parameters a and b. An absorbance-adjusting component of components 1630 may be configured to adjust the reference absorbances using the adjustment parameters, to thereby obtain adjusted reference absorbances $A'_R = a*A*_R + b$; and a second fitting component of components 1630 may be configured to computationally fit, again using statistical software package 1629, the functional relationship described by Eq. (7) between the sample absorbances, the adjusted reference absorbances and the known (spike-in) concentrations to obtain the parameters a, b and A of the calibration curve. Accordingly, when it is desired to calculate an albumin concentration $C_{Alb}$ for a sample under test, given measured absorbances $A_S$ and $A_R$ for the sample, $C_{Alb}$ can be calculated according to $A_S − (a*A_R + b) = A*C_{Alb}$ using the calibration parameters a, b and A obtained by the calibration software components 1630 of system 1600.

Figure 15:
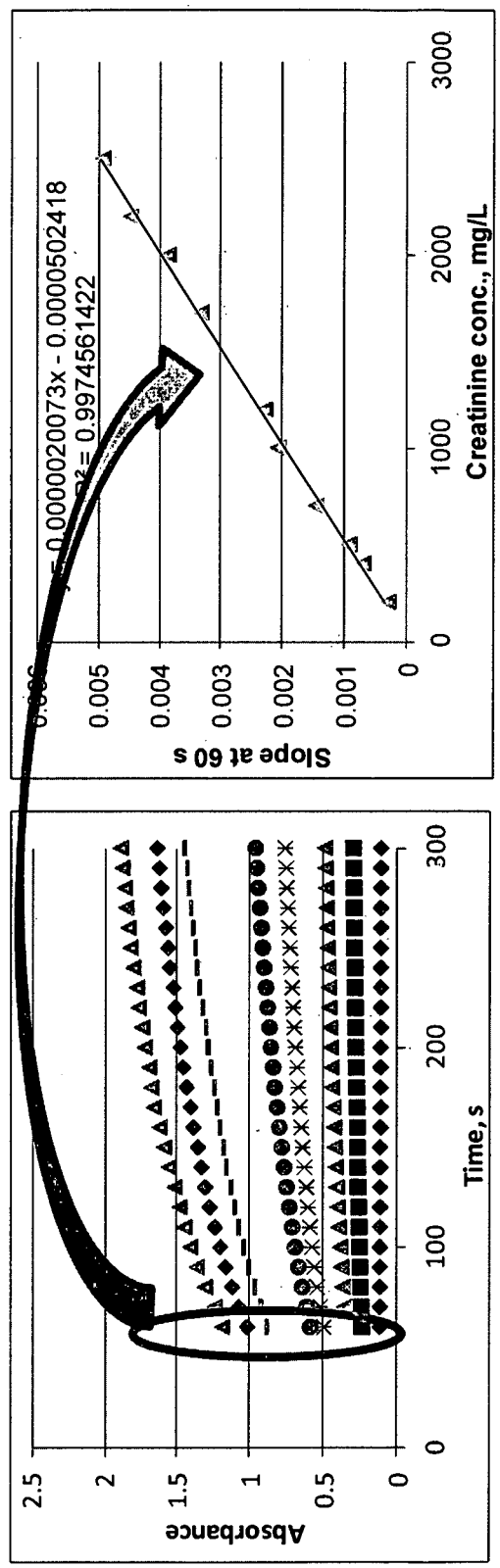

FIG. 15 shows the calibration curve for the creatinine assay. The kinetics of the DNBA/creatinine reaction is measured and a calibration curve for creatinine is generated by plotting the rate of reaction vs. creatinine concentration. Creatinine standards are prepared with artificial or pooled urine and certain concentration of creatinine.

The creatinine assay requires 5 min to 10 min and microalbuminuria assay requires around 5 min.

For the creatinine assay, it will be appreciated that a kinetic measurement may start from the time that the sample is added to the creatinine assay formulation, or that the measurement may be delayed (e.g. for 5 seconds, 10 seconds, 30 seconds, 1 minute, 2 minutes or 5 minutes) before the kinetic measurements are started. Therefore, the actual window of sensing time where the measurements are taken may be from 1 minute to 10 minutes. The time interval for data acquisition during the kinetic measurements in the creatinine assay may be from 0.1 seconds to 15 seconds (e.g. 5 seconds).

Total assay time from sampling to provide ACR value can be less than 10 min, and this is a rapid measurement.

Advantages of Dry Reagent Assay System

The dry-reagents are very easy to be reconstituted by addition of a urine sample.

The reagents allow for a one-step sensing protocol, which significantly improves user-friendliness.

As mentioned hereinbefore, the formulations prevent the formation of air-bubbles adhered to the surface of the cuvette wall upon the reconstitution of the dry-reagent with a urine specimen, allowing direct optical measurement. That is, the formulation disclosed herein allows for fast optical measurement, without having to remove bubbles from the solution (if even possible), the removal of bubbles from the reconstituted formulation in urine also allows for greater accuracy of measuring absorbance, as it reduced light scattering.

When supplied as a dry-reagent, the formulations discussed herein are easy to store and transport, as compared with the wet-reagents.

Operative Variations and Alternatives

The present urinalysis system described above, applying a buffer addition method and/or a protein denaturing method can also be applied for urinary components other than creatinine or albumin. Examples of such analytes include, but is not limited to, water, ions (e.g., sodium, potassium, chloride, phosphoric acid, phosphorus, sulfur, bromide, fluoride, iodide, calcium, magnesium, iron, lead, mercury, etc.), proteins (e.g. haptoglobin, transferrin, immunoglobulin, lactadehydrogenase, gamma-glutamyl transferase, alpha amylase, uropepsinogene, lysozyme, urokinase, etc.), sugars (e.g., glucose, phenylpyruvate, arabinose, xyloseribose, fucose, rhammose, ketopentose, galactose, mannose, fructose, lactose, sucrose, fucosylglucose, raffinose, etc.), amino acids (e.g., alanine, carnosine, glycine, histidine, leucine, lysine, methionine, phenylalanine, serine, tyrosine, valine, hydroxyloproline, galactosylhydroxylyzine, xylosylserine, etc.), hormones (e.g., epinephrine, norepinephrine, dopamine, serotonin, hCG, EFT, estradiol, gonadotropin, corticotropin, prolactin, oxytocin, vasopressin, thyroxine, catecholamines (epinephrine, norepinephrine, dopamine), insulin, erythropoietin, corticosteroids (aldosterone, corticosterone, cortisone), testosterone, progesterone, estrogen, etc.), vitamins (e.g., vitamin B1, vitamin B2, vitamin B6, 4-pyridoxique acid, nicotinic acid, vitamin B]2, biopterine, vitamin C, etc.), drugs or other bioactive substances (e.g., caffeine, cocaine, etc.), metabolic wastes (e.g., urea, uric acid, creatine, choline, piperidine, bilirubin, allantoin, etc.), ketones, folic acid, and the like.

Urinalysis can be performed for human urine with a ranging pH from 5 to 8. Most people have a urine pH that is within this range, but some may be out of the range.

The sensing temperature can be from 15° C. to 40° C.

The dry reagent can be packed within a moisture-proof bag and stored at room temperature for a year at least.

The dry reagent system includes a reagent for reference sample to lessen the effect of pH, temperature and interferences. For creatinine, albumin or other target assay, to include chemical with buffering effect into reagent for reference sample is effective. Especially for albumin assay, denaturing albumin by surfactant in reference sample is highly effective to measure reference sample.

Wet reagents may be used instead of dry reagents. In this case, the wet reagent for measuring creatinine doesn't require a bulking agent, and the wet reagent for measuring microalbuminuria doesn't require non-ionic surfactant 2 as shown in Tables 7 and 8 below.

TABLE 7

| Chemical Category | Range of Concentration Creatinine-Sampling reagent |
|---|---|
| Strong base | 40-80 g/L |
| Buffer | 50-250 g/L |
| Anionic surfactant | 0.1-10 g/L |
| Cationic surfactant | 0.1-10 g/L |
| DNBA | 1-5 g/L |

TABLE 8

| | Range of Concentration | |
|---|---|---|
| Chemical Category | Albumin-Sampling reagent | Albumin-Referencing reagent |
| BCG | 0.1-1.5 g/L | 0.1-1.5 g/L |
| Strong base | 10-50 g/L | 10-50 g/L |
| Buffer | 50-250 g/L | 50-250 g/L |
| Non-ionic surfactant 1 | 1-20 g/L | 1-20 g/L |
| Preservative | 0.1-3 g/L | 0.1-3 g/L |
| Anionic surfactant | 0 w % | 0.1-5 w % (1-50 g/L) |

In addition, the microalbuminuria/creatinine assay can be separated. That is, the microalbuminuria assay may be run alone or the creatinine assay may also be run alone.

The invention claimed is:

1. A method of quantitatively determining a concentration of at least one first analyte in a sample, wherein the at least one first analyte is albumin, the method comprising the steps of:
   (a) adding a portion of the sample to an albumin assay formulation comprising an albumin complexing reagent to generate an albumin sample;
   (b) adding a portion of the sample to an analyte assay reference formulation that is identical to the albumin assay formulation, except that it further comprises a reagent that denatures albumin or blocks a formation of a complex between albumin and the albumin complexing reagent, to generate an analyte reference sample; and
   (c) determining a concentration of albumin in the sample by measuring an absorbance spectra of the albumin sample and analyte reference sample, calculating a difference between the absorbance spectra of the albumin sample and the analyte reference sample and comparing a difference spectrum obtained to a first pre-determined calibration curve of albumin concentration.

2. The method of claim 1, wherein the method further comprises determining a concentration of creatine in the sample, the method comprising the steps of:
   (a) adding a portion of the sample to a creatinine assay formulation comprising a creatinine complexing reagent to generate a creatinine sample; and
   (b) determining a concentration of creatinine in the sample by measuring absorbance spectra of the creatinine in the creatinine sample over a period of time, calculating a rate of an absorbance change of the creatinine sample over said period of time and comparing the rate obtained to a second pre-determined calibration curve of creatinine concentration.

3. The method of claim 2, further comprising the step of determining a albumin/creatinine ratio of the sample.

4. The method of claim 3, wherein one or more of the formulations are lyophilised.

5. The method of claim 2, wherein the creatinine assay sample formulation is an aqueous solution that comprises:
   a compound that reacts with creatinine to generate a creatinine complex;
   a strong base in a concentration of from about 40 to about 80 g/L;
   a buffer in a concentration of from about 50 to about 250 g/L; and
   at least one surfactant in a concentration of from about 0.1 to about 20 g/L.

6. The method of claim 5, wherein the compound that reacts with creatinine to generate a creatinine complex is dinitrobenzoic acid or picric acid.

7. The method of claim 6, wherein the at least one surfactant of the creatinine assay sample formulation comprises an anionic surfactant in a concentration from about 0.1 to about 10 g/L and a cationic surfactant in a concentration from about 0.1 to about 10 g/L.

8. The method of claim 7, wherein a ratio of cationic surfactant:anionic surfactant is 1:5.

9. The method claim 5, wherein the creatinine assay sample formulation is lyophilised.

10. The method of claim 9, wherein the creatinine assay sample formulation further comprises a bulking agent in an amount of from about 1 to about 40 weight % of the formulation.

11. The method of claim 10, wherein the bulking agent is selected from one or more of the group consisting of sugar-mannitol, lactose, and trehalose.

12. The method of claim 9, wherein the creatinine assay sample formulation is lyophilised by a method of preparing a lyophilised formulation for use in an analysis of the creatinine concentration of a sample, the method comprising the steps of:
   (a) mixing the compound, the strong base, the buffer and the at least one surfactant together into a mixture, filtering the mixture, dispensing said mixture into a container and inserting the container into a freeze drying apparatus;

(b) freezing the mixture at a temperature of from about −20° C. to about −80° C. for a period of time ranging from about 0.5 hours to 5 hours;
(c) annealing the mixture at a temperature of from about −10° C. to about −30° C. for a period of time ranging from about 1 hour to 5 hours;
(d) re-freezing the mixture at a temperature of from about −20° C. to about −80° C. for a period of time ranging from about 0.5 hours to 5 hours;
(e) conducting a first drying cycle at a temperature of from about −10° C. to about −30° C. for a period of time ranging from about 5 hours to 50 hours; and
(f) conducting a second drying cycle at a temperature of from about 0° C. to about 60° C. for a period of time ranging from about 1 hour to 20 hours.

13. The method of claim 12, wherein the method further comprises storing the container holding the lyophilised formulation away from light, oxygen and moisture.

14. The method of claim 2, wherein one or more of the formulations are lyophilised.

15. The method of claim 1, wherein the method comprises the steps of:
adding a portion of the sample to each of an:
A) albumin assay sample formulation comprising an albumin complexing reagent to generate an albumin sample; and
B) albumin assay reference formulation that is identical to the albumin assay sample formulation except that it further comprises an anionic surfactant to generate an albumin reference sample.

16. The method of claim 15, wherein the albumin assay sample formulation is an aqueous solution that comprises:
a compound that reacts with albumin to generate an albumin complex in a concentration of from about 0.1 to about 1.5 g/L;
a strong base in a concentration of from about 10 to about 50 g/L;
a buffer in a concentration of from about 50 to about 250 g/L;
a first non-ionic surfactant in a concentration of from about 1 to about 20 g/L; and
a preservative in a concentration of from about 0.1 to about 3 g/L.

17. The method of claim 16, wherein the albumin assay reference formulation comprises each of:
a compound that reacts with albumin to generate an albumin complex;
a strong base;
a buffer;
a first non-ionic surfactant; and
a preservative,
in concentrations that are identical to the albumin assay sample formulation, and further comprises an anionic surfactant.

18. The method of claim 16, wherein the compound that reacts with albumin to generate an albumin complex is bromocresol green.

19. The method of claim 16, wherein the albumin assay sample formulation and the albumin assay reference formulation are lyophilised.

20. The method of claim 19, wherein the albumin assay sample formulation further comprises a second non-ionic surfactant in a concentration of from about 10 to about 200 g/L.

21. The method of claim 20, wherein the albumin assay reference formulation further comprises a second non-ionic surfactant in a concentration that is identical to the albumin assay sample formulation.

22. The method of claim 19, wherein the albumin assay sample formulation and the albumin assay reference formulation are lyophilised by a method of preparing a lyophilised formulation for use in an analysis of albumin concentration of a sample, the method comprising the steps of:
(a) mixing the compound, the strong base, the buffer, the first non-ionic surfactant and the preservative together into a mixture, filtering the mixture, dispensing said mixture into a container and inserting the container into a freeze drying apparatus;
(b) freezing the mixture at a temperature of from about −20° C. to about −80° C. for a period of time ranging from about 0.5 hours to 5 hours;
(c) annealing the mixture at a temperature of from about −10° C. to about −30° C. for a period of time ranging from about 1 hour to 5 hours;
(d) re-freezing the mixture at a temperature of from about −20° C. to about −80° C. for a period of time ranging from about 0.5 hours to 5 hours;
(e) conducting a first drying cycle at a temperature of from about −10° C. to about −30° C. for a period of time ranging from about 5 hours to 50 hours; and
(f) conducting a second drying cycle at a temperature of from about 0° C. to about 60° C. for a period of time ranging from about 1 hour to 20 hours.

23. The method of claim 22, wherein the method further comprises storing the container holding the lyophilised formulation away from light, oxygen and moisture.

24. The method of claim 15, wherein one or more of the formulations are lyophilised.

25. The method of claim 1, wherein one or more of the formulations are lyophilised.

26. The method of claim 1, wherein the first pre-determined calibration curve of albumin concentration is obtained by a computer-implemented method of generating a calibration curve for use in quantitatively determining a concentration of albumin in a urine sample, the computer-implemented method comprising the steps of:
obtaining first absorbance data representing albumin-free sample absorbances and albumin-free reference absorbances for a plurality of albumin-free urine samples; wherein the albumin-free sample absorbances comprise absorbances for respective first portions of the albumin-free urine samples in the presence of an albumin-complexing reagent; and the albumin-free reference absorbances comprise absorbances for respective second portions of the albumin-free urine samples in the presence of the albumin-complexing reagent, and additionally in the presence of an albumin-denaturing reagent or a reagent that blocks a formation of a complex between albumin and the albumin-complexing reagent;
computationally fitting a functional relationship between the albumin-free sample absorbances and the albumin-free reference absorbances to obtain adjustment parameters;
obtaining second absorbance data representing sample absorbances and reference absorbances for a plurality of urine samples having known concentrations of albumin; wherein the sample absorbances comprise absorbances for respective first portions of the urine samples in the presence of the albumin-complexing reagent; and the reference absorbances comprise absorbances for respective second portions of the urine samples in the presence of the albumin-complexing reagent, and additionally in the presence of the albumin-denaturing reagent or the reagent that blocks the formation of a complex between albumin and the albumin-complexing reagent;

adjusting the reference absorbances using the adjustment parameters, to thereby obtain adjusted reference absorbances; and computationally fitting a functional relationship between the sample absorbances, the adjusted reference absorbances and the known concentrations to obtain parameters of the calibration curve.

27. The method according to claim 26, wherein the functional relationship between the albumin-free sample absorbances and the albumin-free reference absorbances is of a first form $A_S^0 = a*A_R^0 + b$, where $A_S^0$ are the albumin-free sample absorbances, $A_R^0$ are the albumin-free reference absorbances, and a and b are the adjustment parameters.

28. The method according to claim 27, wherein the adjusted reference absorbances are calculated according to $a*A_R^* + b$, where $A_R^*$ are the reference absorbances.

29. The method according to claim 28, wherein the functional relationship between the sample absorbances, the adjusted reference absorbances and the known concentrations is of a second form $A_S^* - (a*A_R^* + b) = A*C_{Alb}^*$, where $A_S^*$ are the sample absorbances, and $C_{Alb}^*$ are the known concentrations, such that a, b and A are the parameters of the calibration curve.

* * * * *